US007620455B2

(12) United States Patent
Maschino

(10) Patent No.: US 7,620,455 B2
(45) Date of Patent: Nov. 17, 2009

(54) CRANIAL NERVE STIMULATION TO TREAT EATING DISORDERS

(75) Inventor: Steven E. Maschino, Seabrook, TX (US)

(73) Assignee: Cyberonics, Inc., Houston, TX (US)

( * ) Notice: Subject to any disclaimer, the term of this patent is extended or adjusted under 35 U.S.C. 154(b) by 494 days.

(21) Appl. No.: 11/258,764

(22) Filed: Oct. 25, 2005

(65) Prior Publication Data

US 2007/0093870 A1 Apr. 26, 2007

(51) Int. Cl.
*A61N 1/36* (2006.01)
(52) U.S. Cl. ........................................... 607/40
(58) Field of Classification Search ............ 607/40
See application file for complete search history.

(56) References Cited

U.S. PATENT DOCUMENTS

| | | | |
|---|---|---|---|
| 3,796,221 A | 3/1974 | Hagfors | 128/421 |
| 4,305,402 A | 12/1981 | Katims | 128/741 |
| 4,338,945 A | 7/1982 | Kosugi | 128/421 |
| 4,431,000 A | 2/1984 | Butlet et al. | 128/421 |
| 4,503,863 A | 3/1985 | Katims | 128/741 |
| 4,541,432 A | 9/1985 | Molina-Nego et al. | 128/421 |
| 4,573,481 A | 3/1986 | Bullara | 128/784 |
| 4,592,339 A | 6/1986 | Kuzmak et al. | 128/1 R |
| 4,702,254 A | 10/1987 | Zabara | 128/421 |
| 4,793,353 A | 12/1988 | Borkan | 128/421 |
| 4,867,164 A | 9/1989 | Zabara | 128/421 |
| 4,920,979 A | 5/1990 | Bullara | 128/784 |
| 4,977,985 A | 12/1990 | Wells et al. | 188/71.1 |
| 4,979,511 A | 12/1990 | Terry, Jr. | 128/642 |
| 5,025,807 A | 6/1991 | Zabara | 128/421 |
| 5,074,868 A | 12/1991 | Kuzmak | 606/157 |
| 5,081,987 A | 1/1992 | Nigam | 120/419 |
| 5,154,172 A | 10/1992 | Terry, Jr. et al. | 128/419 |
| 5,188,104 A | 2/1993 | Wernicke et al. | 128/419 |
| 5,205,285 A | 4/1993 | Baker, Jr. | 128/423 |
| 5,215,086 A | 6/1993 | Terry, Jr. et al. | 128/421 |
| 5,226,429 A | 7/1993 | Kuzmak | 128/898 |
| 5,231,988 A | 8/1993 | Wernicke et al. | 128/421 |
| 5,263,480 A * | 11/1993 | Wernicke et al. | 607/118 |
| 5,269,303 A | 12/1993 | Wernicke et al. | 607/45 |
| 5,299,569 A | 4/1994 | Wernicke et al. | 607/45 |
| 5,304,206 A | 4/1994 | Baker, Jr. et al. | 607/2 |
| 5,311,876 A | 5/1994 | Olsen et al. | 128/731 |
| 5,330,515 A | 7/1994 | Rutecki et al. | 607/46 |
| 5,335,657 A | 8/1994 | Terry, Jr. et al. | 607/45 |
| 5,423,872 A | 6/1995 | Cigaina | 607/40 |

(Continued)

FOREIGN PATENT DOCUMENTS

EP 1145736 4/2004

OTHER PUBLICATIONS

Ritter, Sue et al.; Neuroanatomy and Physiology of Abdominal Vagal Afferents; Andrews, P.L.R., et al; *A Protective Role for Vagal Afferents: An Hypothesis;* Chapter 12 pp. 281-302; (2001).

(Continued)

*Primary Examiner*—Mark W Bockelman
*Assistant Examiner*—Eric D. Bertram
(74) *Attorney, Agent, or Firm*—Williams, Morgan & Amerson P.C.; Timothy L. Scott

(57) ABSTRACT

Methods and systems of treating a patient having an eating disorder involving coupling at least one electrode to at least one cranial nerve of the patient, implanting a sensory stimulation device in the patient, applying a sensory stimulus to the patient using the sensory stimulation device, detecting the patient's response to the sensory stimulus, and applying an electrical signal to the cranial nerve using the electrode after detecting the response to treat the eating disorder. The methods and systems are effective in treating bulimia.

7 Claims, 17 Drawing Sheets

U.S. PATENT DOCUMENTS

| | | | |
|---|---|---|---|
| 5,540,730 A | 7/1996 | Terry, Jr. et al. | 607/40 |
| 5,540,734 A | 7/1996 | Zabara | 607/46 |
| 5,601,604 A | 2/1997 | Vincent | 606/216 |
| 5,645,570 A | 7/1997 | Corbucci | 607/5 |
| 5,690,688 A | 11/1997 | Noren et al. | 607/17 |
| 5,690,691 A | 11/1997 | Chen et al. | 607/40 |
| 5,702,429 A | 12/1997 | King | 607/46 |
| 5,771,903 A | 6/1998 | Jakobsson | 128/898 |
| 5,792,186 A | 8/1998 | Rise | 607/2 |
| 5,792,212 A | 8/1998 | Weijand | 607/73 |
| 5,800,474 A | 9/1998 | Benabid et al. | 607/45 |
| 5,836,994 A | 11/1998 | Bourgeois | 607/40 |
| 5,861,014 A | 1/1999 | Familoni | 607/40 |
| 5,913,882 A | 6/1999 | King | 607/62 |
| 5,919,216 A | 7/1999 | Houben et al. | 607/72 |
| 5,928,272 A | 7/1999 | Adkins et al. | 607/45 |
| 5,995,868 A | 11/1999 | Dorfmeister et al. | 600/544 |
| 5,995,872 A | 11/1999 | Bourgeois | 607/40 |
| 6,016,449 A | 1/2000 | Fischell et al. | 607/45 |
| 6,018,682 A | 1/2000 | Rise | 607/45 |
| 6,044,846 A | 4/2000 | Edwards | 128/898 |
| 6,061,593 A | 5/2000 | Fischell et al. | 600/544 |
| 6,083,249 A | 7/2000 | Familoni | 607/40 |
| 6,091,992 A | 7/2000 | Bourgeois et al. | 607/40 |
| 6,092,528 A | 7/2000 | Edwards | 128/898 |
| 6,097,984 A | 8/2000 | Douglas | 607/40 |
| 6,102,922 A | 8/2000 | Jakobsson et al. | 606/157 |
| 6,104,955 A | 8/2000 | Bourgeios | 606/40 |
| 6,104,956 A | 8/2000 | Naritoku et al. | 607/45 |
| 6,115,635 A | 9/2000 | Bourgeois | 607/40 |
| 6,128,538 A | 10/2000 | Fischell et al. | 607/45 |
| 6,129,685 A | 10/2000 | Howard, III | 600/585 |
| 6,132,361 A | 10/2000 | Epstein et al. | 600/13 |
| 6,134,474 A | 10/2000 | Fischell et al. | 607/45 |
| 6,141,590 A | 10/2000 | Renirie et al. | 607/20 |
| 6,216,039 B1 | 4/2001 | Bourgeous | 607/40 |
| 6,248,080 B1 | 6/2001 | Miesel et al. | 600/561 |
| 6,253,109 B1 | 6/2001 | Gielen | 607/45 |
| 6,295,472 B1 | 9/2001 | Rubinstein et al. | 607/55 |
| 6,304,775 B1 | 10/2001 | Iasemidis et al. | 600/544 |
| 6,321,124 B1 | 11/2001 | Cigaina | 607/133 |
| 6,327,503 B1 | 12/2001 | Familoni | 607/40 |
| 6,337,997 B1 | 1/2002 | Rise | 607/45 |
| 6,339,725 B1 | 1/2002 | Naritoku et al. | 607/45 |
| 6,341,236 B1 | 1/2002 | Osorio et al. | 607/45 |
| 6,353,762 B1 | 3/2002 | Baudino et al. | 607/45 |
| 6,356,784 B1 | 3/2002 | Lozano et al. | 607/2 |
| 6,405,732 B1 | 6/2002 | Edwards et al. | 128/898 |
| 6,463,328 B1 | 10/2002 | John | 607/45 |
| 6,473,639 B1 | 10/2002 | Fischell et al. | 600/544 |
| 6,473,644 B1 | 10/2002 | Terry, Jr. et al. | 607/2 |
| 6,480,743 B1 | 11/2002 | Kirkpatrick et al. | 607/45 |
| 6,510,332 B1 | 1/2003 | Greenstein | 600/377 |
| 6,532,388 B1 | 3/2003 | Hill et al. | 607/2 |
| 6,535,764 B2 | 3/2003 | Imran et al. | 607/45 |
| 6,542,776 B1 | 4/2003 | Gordon et al. | 607/40 |
| 6,549,804 B1 | 4/2003 | Osorio et al. | 600/54 |
| 6,556,868 B2 | 4/2003 | Naritoku et al. | 607/45 |
| 6,564,101 B1 | 5/2003 | Zikria | 607/40 |
| 6,587,727 B2 | 7/2003 | Osorio et al. | 607/45 |
| 6,591,137 B1 | 7/2003 | Fischell et al. | 607/40 |
| 6,594,524 B2 | 7/2003 | Esteller et al. | 607/45 |
| 6,600,953 B2 | 7/2003 | Flesler et al. | 607/40 |
| 6,606,518 B1 | 8/2003 | Cigaina | 607/41 |
| 6,606,523 B1 | 8/2003 | Jenkins | 607/133 |
| 6,609,025 B2 | 8/2003 | Barrett et al. | 607/2 |
| 6,610,713 B2 | 8/2003 | Tracey | 514/343 |
| 6,611,715 B1 | 8/2003 | Boveja | 607/40 |
| 6,612,983 B1 | 9/2003 | Marchal | 600/300 |
| 6,615,081 B1 | 9/2003 | Boveja | 607/2 |
| 6,615,084 B1 | 9/2003 | Cigaina | 607/40 |
| 6,622,038 B2 | 9/2003 | Barrett et al. | 607/2 |
| 6,622,041 B2 | 9/2003 | Terry, Jr. et al. | 607/9 |
| 6,622,047 B2 | 9/2003 | Barrett et al. | 607/45 |
| 6,647,296 B2 | 11/2003 | Fischell et al. | 607/45 |
| 6,650,943 B1 | 11/2003 | Whitehurst et al. | 607/39 |
| 6,671,555 B2 | 12/2003 | Gielen et al. | 607/45 |
| 6,671,556 B2 | 12/2003 | Osorio et al. | 607/45 |
| 6,684,104 B2 | 1/2004 | Gordon et al. | 607/40 |
| 6,684,105 B2 | 1/2004 | Cohen et al. | 607/63 |
| 6,690,974 B2 | 2/2004 | Archer et al. | 607/45 |
| 6,708,064 B2 | 3/2004 | Rezai | 607/45 |
| 6,721,603 B2 | 4/2004 | Zabara et al. | 607/46 |
| 6,735,474 B1 | 5/2004 | Loeb et al. | 607/41 |
| 6,754,536 B2 | 6/2004 | Swoyer et al. | 607/40 |
| 6,760,626 B1 | 7/2004 | Boveja | 607/59 |
| 6,768,969 B1 | 7/2004 | Nikitin et al. | 702/188 |
| 6,775,573 B2 | 8/2004 | Schuler et al. | 607/40 |
| 6,819,956 B2 | 11/2004 | DiLorenzo | 607/45 |
| 6,826,428 B1 | 11/2004 | Chen et al. | 607/40 |
| 6,832,114 B1 | 12/2004 | Whitehurst et al. | 607/40 |
| 6,853,862 B1 | 2/2005 | Marchal et al. | 607/40 |
| 6,885,888 B2 | 4/2005 | Rezai | 607/9 |
| 6,889,076 B2 | 5/2005 | Cigaina | 600/547 |
| 6,895,278 B1 | 5/2005 | Gordon | 607/40 |
| 6,907,295 B2 | 6/2005 | Gross et al. | 607/118 |
| 6,908,487 B2 | 6/2005 | Cigaina | 623/23.67 |
| 6,920,357 B2 | 7/2005 | Osorio et al. | 607/45 |
| 6,944,501 B1 | 9/2005 | Pless | 607/45 |
| 6,961,618 B2 | 11/2005 | Osorio et al. | 607/45 |
| 7,006,872 B2 | 2/2006 | Gielen et al. | 607/45 |
| 7,050,856 B2 | 5/2006 | Stypulkowski | 607/45 |
| 7,054,686 B2 | 5/2006 | MacDonald | 607/9 |
| 2002/0116030 A1 | 8/2002 | Rezai | 607/9 |
| 2003/0181954 A1 | 9/2003 | Rezai | 607/45 |
| 2003/0208212 A1 | 11/2003 | Cigaina | 606/151 |
| 2004/0167583 A1 | 8/2004 | Knudson et al. | 607/40 |
| 2004/0172085 A1 | 9/2004 | Knudson et al. | 607/40 |
| 2004/0172094 A1 | 9/2004 | Cohen et al. | 607/48 |
| 2004/0176812 A1 | 9/2004 | Knudson et al. | 607/40 |
| 2004/0210274 A1 | 10/2004 | Bauhahn et al. | 607/60 |
| 2005/0010262 A1 | 1/2005 | Rezai et al. | 607/46 |
| 2005/0021092 A1 | 1/2005 | Yun et al. | 607/3 |
| 2005/0021103 A1 | 1/2005 | DiLorenzo | 607/45 |
| 2005/0021104 A1 | 1/2005 | DiLorenzo | 607/45 |
| 2005/0038484 A1 | 2/2005 | Knudson et al. | 607/40 |
| 2005/0049655 A1 | 3/2005 | Boveja et al. | 607/58 |
| 2005/0060007 A1 | 3/2005 | Goetz | 607/48 |
| 2005/0060008 A1 | 3/2005 | Goetz | 607/48 |
| 2005/0060010 A1 | 3/2005 | Goetz | 607/48 |
| 2005/0065575 A1 | 3/2005 | Dobak | 607/45 |
| 2005/0119703 A1 | 6/2005 | DiLorenzo | 607/2 |
| 2005/0131485 A1 | 6/2005 | Knudson et al. | 607/40 |
| 2005/0131486 A1 | 6/2005 | Boveja et al. | 607/40 |
| 2005/0154425 A1 | 7/2005 | Boveja et al. | 607/45 |
| 2005/0192644 A1 | 9/2005 | Boveja et al. | 607/45 |

OTHER PUBLICATIONS

Ritter, Sue et al.; Neuroanatomy and Physiology of Abdominal Vagal Afferents; Rogers, R.C., et al.; *Central Regulation of Brainstem Gastric Vago-Vagal Control Circuits;* Chapter 5, pp. 100-134; (2001).

Ritter, Sue et al.; Neuroanatomy and Physiology of Abdominal Vagal Afferents; *Participation of Vagal Sensory Neurons in Putatitve Satiety Signals From the Upper Gastrointestinal Tract,* Chapter 10, pp. 222-248; (2001).

T. R.Henry, M.D.;et al.; *Therapeutic Mechanisms of Vagus Nerve Stimulation;* Neurology 59 (Suppl 4) (2002); pp. S3-S14.

Terry, R.S., et al.; *The Implantable Neurocybernetic Prosthesis System;* PACE, vol. 14, No. 1, Jan. 1991; pp. 86-93.

Bachman, D.S., et al.; *Effects of Vagal Volleys and Serotonin on Units of Cingulate Cortex in Monkeys;* Laboratory of Brain Evolution and Behavior, National Institute of Mental Health; 1976; pp. 253-269.

Hallowitz, R.A., et al.; *Effects of Vagal Volleys on Units of Intralaminar and Juxtalaminar Thalamic Nuclei in Moneys;* Brain Research, 130 (1976); pp. 271-286.

Lockhard, J.S., et al.; *Feasibility and Safety of Vagal Stimulation in Monkey Model;* Epilepsia, vol. 31, Suppl. 2, (1990); pp. S20-S26.

Malow, B.S., et al.; *Vagus Nerve Stimulation Reduces Daytime Sleepiness in Epilepsy Patients;* Neurology 57, (2001); pp. 879-884.

DeGiorgio, C.M., et al.; *Vagus Nerve Stimulation: Analysis of Device Parameters in 154 Patients During the Long-Term XE5 Study;* Epilepsia, vol. 42, No. 8 (2001); pp. 1017-1020.

Clark, K.B., et al.; Nature Neuroscience; *Enhanced Recognition Memory Following Vagus Nerve Stimulation in Human Subjects;* Reprinted from Nature Neuroscience, vol. 2, No. 1 (1999); pp. 94-98.

Dodrill, C.B., et al.; *Effects of Vagal Nerve Stimulation on Cognition and Quality of Life in Epilepsy;* Epilepsy & Behavior 2, pp. 46-53 (2001).

Valdes-Cruz, A., et al.; *Chronic Stimulation of the Cat Vagus Nerve Effect on Sleep and Behavior;* Progress in Neuro-Psychopharmacology & Biological Psychiatry 26 (2002); pp. 114-118.

Vonck, K., et al.; *The Mechanism of Action of Vagus Nerve Stimulation for Refractory Epilepsy;* Journal of Neurophysiology, vol. 18, No. 5 (2001); pp. 394-401.

Woodbury, J.W., et al.; *Vagal Stimulation Reduces the Severity of Maximal Electroshock Seizures in Intact Rats: Use of a Cuff Electrode for Stimulating and Recording;* PACE, vol. 14, (1991); pp. 94-107.

Epstein, S.F., et al.; *Treatment of Angina Pectoris by Electrical Stimulation of the Carotid-Sinus Nerves;* The New England Journal of Medicine, vol. 280, No. 18 (1969); pp. 971-978.

Kriwanek, S., et al.; *Therapeutic Failures After Gastric Bypass Operations for Morbid Obesity;* Langenbecks Arch Chir (1995) 380: pp. 70-74.

Brownel, K.D., et al.; Eating Disorders and Obesity: A Comprehensive Handbook; Leibowitz, S.F.; *Central Physiological Determinants of Eating Behavior and Weight;* pp. 3-7.

Grundy, D., et al.; Handbook of Physiology-The Gastrointestinal System I—*Sensory Afferents from the Gastrointestinal Tract;* Chapter 16; pp. 593-619.

* cited by examiner

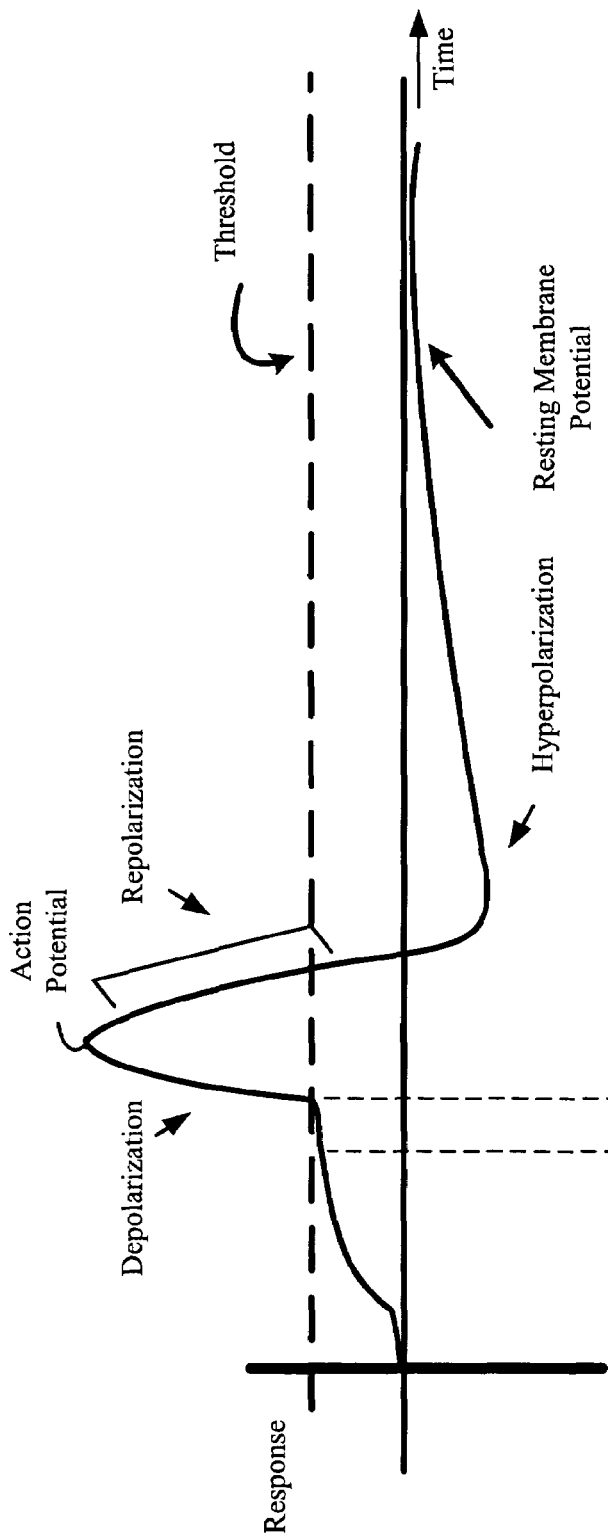
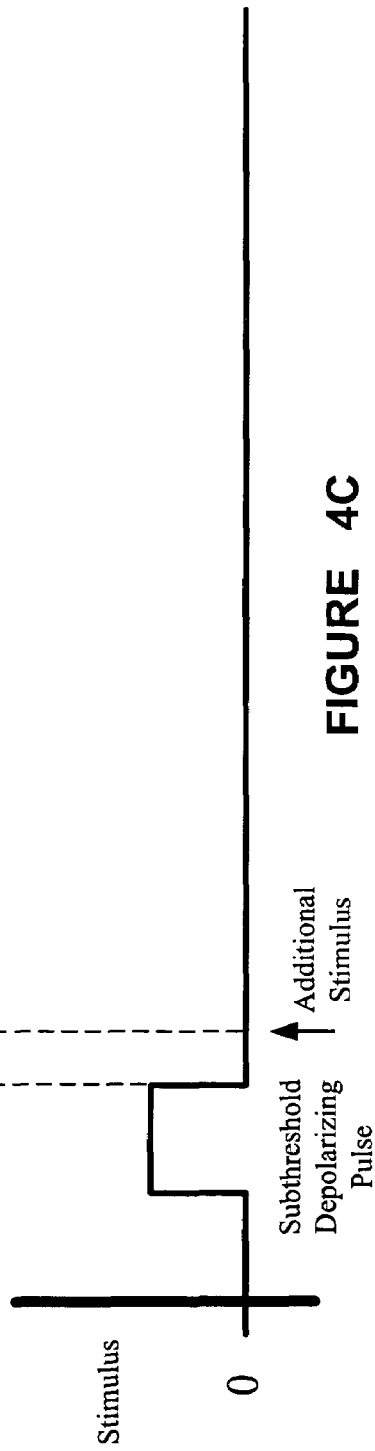
FIGURE 4B
FIGURE 4C

CRANIAL NERVE STIMULATION TO TREAT EATING DISORDERS

BACKGROUND OF THE INVENTION

1. Field of the Invention

The present invention relates generally to methods and apparatus for treating disorders by using cranial nerve stimulation. More particularly, it concerns methods and apparatus for treating eating disorders, such as bulimia, by using vagus nerve stimulation.

2. Description of the Related Art

The human nervous system (HNS) includes the brain and the spinal cord, collectively known as the central nervous system (CNS). The central nervous system comprises nerve fibers. The network of nerves in the remaining portions of the human body forms the peripheral nervous system (PNS). Some peripheral nerves, known as cranial nerves, connect directly to the brain to control various brain functions, such as vision, eye movement, hearing, facial movement, and feeling. Another system of peripheral nerves, known as the autonomic nervous system (ANS), controls blood vessel diameter, intestinal movements, and actions of many internal organs. Autonomic functions include blood pressure, body temperature, heartbeat and essentially all the unconscious activities that occur without voluntary control.

Like the rest of the human nervous system, nerve signals travel up and down the peripheral nerves, which link the brain to the rest of the human body. Nerve tracts or pathways, in the brain and the peripheral nerves are sheathed in a covering called myelin. The myelin sheath insulates electrical pulses traveling along the nerves. A nerve bundle may comprise up to 100,000 or more individual nerve fibers of different types, including larger diameter A and B fibers which comprise a myelin sheath and C fibers which have a much smaller diameter and are unmyelinated. Different types of nerve fibers, among other things, comprise different sizes, conduction velocities, stimulation thresholds, and myelination status (i.e., myelinated or unmyelinated).

Gastrointestinal functions are controlled by various cranial nerves that traverse portions of the human body. For example, cranial nerve X (i.e., the vagus nerve) traverses the esophagus and the stomach. Below the roots of the lungs, the vagus nerve diverges into various parts, which innervate the esophagus region. Traversing the esophagus downward, the vagus nerve divides and reunites to form open meshed formations known as the esophageal plexus. The esophageal plexus contains small ganglia. Much of the branches of the right vagus nerve incline posteriorly while most of the left vagus nerves incline anteriorly. The esophageal plexus also includes thoracic portions of the sympathetic nerve trunks, e.g., the thoracic splanchnic nerves. Below the esophageal plexus, the vagus nerve traverses to form the gastric branches of the anterior and the posterior vagus trunks.

There are various disorders relating to the gastrointestinal system, including various gastrointestinal-related and eating diseases. Motility disorder is a gastrointestinal disorder that the causes muscular contractions of the esophagus that guide food to the stomach to become dis-coordinated or weak. This interferes with movement of food and fluid down the esophagus. Other eating disorders include anorexia nervosa, which is a disorder that is characterized by the restriction of food and the refusal to maintain a minimal normal body weight. Another eating disorder is bulimia nervosa, which is characterized by addictive binge-purge cycles. A bulimic person eats compulsively and then purges through self-induced vomiting or involuntary vomiting.

Yet another disorder/eating disorder includes compulsive overeating, which is characterized by vicious cycles of binge eating and depression. Another gastrointestinal or eating disorder includes binge overeating. In the case of binge overeating, nerve signals indicative of the fact that a person is full may not register in the brain. Various age-groups of people are affected by eating disorders and other gastrointestinal disorders. Treatments to address these disorders include physiological treatments, such as drug treatments, as well as psychological treatments, such as counseling. Besides drug regimens, invasive medical procedures, and/or counseling, effective treatment of such diseases and disorders are fairly limited. Further, certain patients may not react favorably to various types of drugs or other treatments.

The present invention is directed to overcoming, or at least reducing, the effects of one or more of the problems set forth above.

SUMMARY OF THE INVENTION

In one embodiment, the present invention relates to a method of treating a patient having an eating disorder including coupling at least one electrode to at least one vagus nerve of the patient, implanting a sensory stimulation device in the patient, applying a sensory stimulus to the patient using the sensory stimulation device, detecting the patient's response to the sensory stimulus, and applying an electrical signal to the vagus nerve using the electrode after detecting the response to treat the eating disorder.

In another embodiment, the present invention relates to a method of treating a patient having an eating disorder including coupling at least one electrode to at least one vagus nerve of the patient, providing a programmable electrical signal generator coupled to the electrode, generating an electrical signal with the electrical signal generator, applying the electrical signal to the electrode to treat the eating disorder, implanting a sensory stimulation device in the patient, applying a sensory stimulus to the patient, and detecting the patient's response to the sensory stimulus, wherein the applying the electrical signal to the vagus nerve is initiated after detecting the response.

In another embodiment, the present invention relates to a computer readable program storage device encoded with instructions that, when executed by a computer, perform a method including applying a sensory stimulus to a patient, detecting the patient's response to the sensory stimulus, generating an electrical signal, and providing the electrical signal to a vagus nerve of the patient by using an electrode to treat an eating disorder, wherein the providing the electrical signal is initiated after detecting the response.

In another embodiment, the present invention relates to an eating disorder treatment system including at least one electrode coupled to at least one vagus nerve of a patient, an implantable device operatively coupled to the electrode and comprising an electrical signal generator capable of applying an electrical signal to the vagus nerve using the electrode to treat the eating disorder, and a sensory stimulus device capable of applying a sensory stimulus to the patient.

In one embodiment, the present invention relates to a method of treating a patient having an eating disorder including applying a sensory stimulus to the patient using the implantable medical device, detecting the patient's response to the sensory stimulus, determining if a tolerance level has been reached based upon the patient's response, and applying an electrical signal to a portion of a vagus nerve of the patient to treat the eating disorder based upon the tolerance level.

In one embodiment, the present invention relates to a method of treating a patient having an eating disorder including applying a stimulus to said patient using said implantable medical device; detecting at least one response selected from the group consisting of refractory period, latency, synaptic latency, synaptic jitter, and conduction delay resulting from said stimulus; comparing said at least one response resulting from said stimulus to at least one response associated with a predetermined threshold to detect a change in said response; and applying an electrical signal to a portion of a vagus nerve of said patient based upon said change in said response.

BRIEF DESCRIPTION OF THE DRAWINGS

The invention may be understood by reference to the following description taken in conjunction with the accompanying drawings, in which like reference numerals identify like elements, and in which:

FIG. 4B illustrates an exemplary electrical signal response of a firing neuron as a graph of voltage at a given location at particular times during firing by the neurostimulator of FIG. 2, when applying a sub-threshold depolarizing pulse and additional stimulus to the vagus nerve, in accordance with one illustrative embodiment of the present invention;

FIG. 4C illustrates an exemplary stimulus including a sub-threshold depolarizing pulse and additional stimulus to the vagus nerve for firing a neuron as a graph of voltage at a given location at particular times by the neurostimulator of FIG. 2, in accordance with one illustrative embodiment of the present invention;

Figure 1:
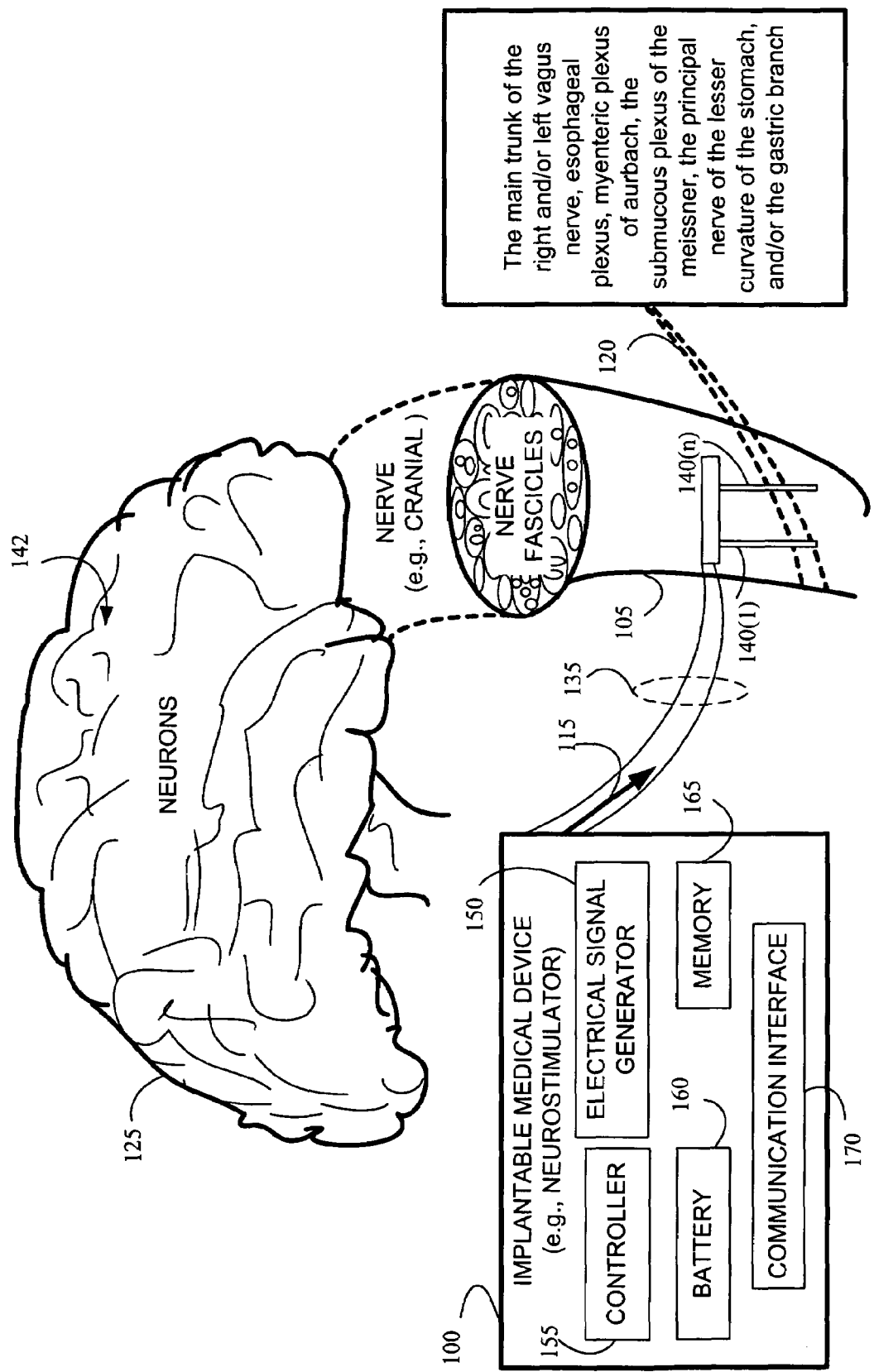
FIG. 1 is a stylized schematic representation of an implantable medical device that stimulates a cranial nerve for treating a patient with an eating disorder, according to one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DESCRIPTION OF ILLUSTRATIVE EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

Certain terms are used throughout the following description and claims refer to particular system components. As one skilled in the art will appreciate, components may be referred to by different names. This document does not intend to distinguish between components that differ in name but not function. In the following discussion and in the claims, the terms "including" and "including" are used in an open-ended fashion, and thus should be interpreted to mean "including, but not limited to." Also, the term "couple" or "couples" is intended to mean either a direct or an indirect electrical connection. For example, if a first device couples to a second device, that connection may be through a direct electrical connection or through an indirect electrical connection via other devices, biological tissues, or magnetic fields. "Direct contact," "direct attachment," or providing a "direct coupling" indicates that a surface of a first element contacts the surface of a second element with no substantial attenuating medium therebetween. The presence of substances, such as bodily fluids, that do not substantially attenuate electrical connections does not vitiate direct contact. The word "or" is used in the inclusive sense (i.e., "and/or") unless a specific use to the contrary is explicitly stated.

Embodiments of the present invention provide for the treatment of eating disorder(s) by stimulation of cranial nerves, such as the vagus nerves, trigeminal nerves, accessory nerves, or hypoglossal nerves. Embodiments of the present invention provide for an electrical stimulation of a portion of a cranial nerve to treat an eating disorder. Eating disorders may be treated using the electrical stimulation provided by an implantable medical device (IMD). Eating disorders may include anorexia nervosa, bulimia nervosa, compulsive overeating, and binge overeating, among others. In one embodiment, the present invention relates to the treatment of bulimia. Embodiments of the present invention provide for monitoring a feedback or biofeedback from a patient or an external source in response to a sensory signal. Based upon the feedback or biofeedback, an adjustment to subsequent stimulation may be performed.

Cranial nerve stimulation has been used to treat a number of nervous system disorders, including epilepsy and other movement disorders, depression and other neuropsychiatric disorders, dementia, coma, migraine headache, obesity, eating disorders, sleep disorders, cardiac disorders (such as congestive heart failure and atrial fibrillation), hypertension, endocrine disorders (such as diabetes and hypoglycemia), and pain, among others. See, e.g., U.S. Pats. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the recognition that cranial nerve stimulation may be an appropriate treatment for the foregoing conditions, the fact that detailed neural pathways for many (if not all) cranial nerves remain relatively unknown makes predictions of efficacy for any given disorder difficult. Even if such pathways were known, moreover, the precise stimulation parameters that would energize particular pathways that affect the particular disorder likewise are difficult to predict. Accordingly, cranial nerve stimulation, and particularly vagus nerve stimulation, has not heretofore been deemed appropriate for use in treating eating disorders.

In one embodiment of the present invention, methods, apparatus, and systems stimulate an autonomic nerve, such as a cranial nerve, e.g., a vagus nerve, using an electrical signal to treat an eating disorder. "Electrical signal" on the nerve refers to electrical activity (i.e., a pulsed or non-pulsed electrical current) that is applied to the nerve from a source external to the nerve, e.g., an implanted neurostimulator. In general, the term "electrical signal" thus refers to an exogenous electrical signal generated by the implanted medical device and applied to a nerve, in contrast to native electrical activity comprising afferent and efferent action potentials, hyperpolarizations, and sub-threshold depolarizations that are generated by the patient's body. Disclosed herein is a method for treating an eating disorder using stimulation of the vagus nerve (cranial nerve X). A generally suitable form of neurostimulator for use in the method and apparatus of the present invention is disclosed, for example, in U.S. Pat. No. 5,154,172, assigned to the same assignee as the present application. A commercially available neurostimulator system referred to as a VNS Therapy™ Pulse Generator is available from Cyberonics, Inc., Houston, Tex., the assignee of the present application. Certain parameters of the electrical signal generated by the neurostimulator are programmable, such as by means of an external programmer in a manner conventional for implantable electrical medical devices.

Embodiments of the present invention provide for an electrical stimulation of a portion of an autonomic nerve to treat an eating or eating disorder. A portion of a cranial nerve (e.g., a vagus nerve), such as the esophageal plexus, the myenteric plexus of Auerbach, the submucosal plexus of Meissner, and other portions of the gastric branches of the vagus nerve may be stimulated to affect eating functions or eating disorders. Stimulation of a portion of the vagus nerve may be used to modify various eating disorders (e.g., motility disorder, anorexia nervosa, bulimia nervosa, compulsive overeating, binge overeating, etc.). Stimulation of the esophageal plexus may include sympathetic and parasympathetic nerve stimulation. Additionally, afferent, efferent or afferent-efferent combination stimulation may be performed to treat eating disorders. The stimulation performed by embodiments of the present invention may include stimulation, blocking nerve conduction, or stimulation in combination with blocking, of various electrical signals on various nerve paths, in order to treat eating disorders.

Turning now to FIG. 1, an implantable medical device (IMD) 100 is provided for stimulating a nerve, such as an autonomic nerve 105 of a patient to treat an eating disorder using neurostimulation, according to one illustrative embodiment of the present invention. The term "autonomic nerve" refers to any portion of the main trunk or any branch of a cranial nerve including cranial nerve fibers, a left cranial nerve and a right cranial nerve, or any portion of the nervous system that is related to regulating the viscera of the human body. The IMD 100 may deliver an electrical signal 115 to a nerve branch 120 of the autonomic nerve 105 that travels to the brain 125 of a patient. The nerve branch 120 provides the electrical signal 115 to the gastrointestinal system of a patient. The nerve branch 120 may be a nerve branch of the nerve branch 120 that is associated with the parasympathetic control or the sympathetic control of gastrointestinal function.

The IMD 100 may apply neurostimulation by delivering the electrical signal 115 to the nerve branch 120 via a lead 135 coupled to one or more electrodes 140 (1-n). For example, the IMD 100 may stimulate the autonomic nerve 105 by applying the electrical signal 115 to the nerve branch 120 that couples to the main trunk of the right or left vagus nerve, the esophageal plexus, the myenteric plexus of Auerbach, the submucosal plexus of Meissner, the principal nerve of the lesser curvature of the stomach, or the gastric branch, using the electrode(s) 140(1-n). The IMD 100 may also stimulate a portion of the brain 125 directly innervated by the autonomic nerve 105 or indirectly innervated by the autonomic nerve 105. Such portions of the brain may include the hypothalamus, the thalamus, the cingulated, and the insula, among others.

Consistent with one embodiment of the present invention, the IMD 100 may be a neurostimulator device capable of treating a disease, disorder or condition relating to the eating functions of a patient by providing electrical neurostimulation therapy to a patient. In order to accomplish this task, the IMD 100 may be implanted in the patient at a suitable location. The IMD 100 may apply the electrical signal 115, which may comprise an electrical pulse signal, to the autonomic nerve 105. The IMD 100 may generate the electrical signal 115 defined by one or more characteristics. These characteristics may be compared to one or more corresponding values within a predetermined range. The IMD 100 may apply the electrical signal 115 to the nerve branch 120 or a nerve fascicle within the autonomic nerve 105. By applying the electrical signal 115, the IMD 100 may treat an eating disorder in a patient.

Implantable medical devices 100 that may be used in the present invention include any of a variety of electrical stimulation devices, such as a neurostimulator capable of stimulating a neural structure in a patient, especially for stimulating a patient's autonomic nerve, such as a vagus nerve. The IMD 100 is capable of delivering a controlled current stimulation signal. Although the IMD 100 is described in terms of autonomic nerve stimulation, and particularly vagus nerve stimulation, a person of ordinary skill in the art would recognize that the present invention is not so limited. For example, the IMD 100 may be applied to the stimulation of other autonomic nerves, sympathetic or parasympathetic, afferent or efferent, or other neural tissue, such as one or more brain structures of the patient.

In the generally accepted clinical labeling of cranial nerves, the tenth cranial nerve is the vagus nerve, which originates from the brainstem of the brain 125. The left and right vagus nerves emerge from the corresponding side of the brainstem. The vagus nerves pass through the foramina of the skull to parts of the head, neck and trunk. Left and right vagus nerves include both sensory and motor nerve fibers. The cell bodies of vagal sensory nerve fibers are located outside the brain 125 in ganglia groups, and the cell bodies of vagal motor nerve fibers are attached to neurons 142 located within the brain 125. The vagus nerve is a parasympathetic nerve, part of the peripheral nervous system (PNS). Somatic nerve fibers of the cranial nerves are involved in conscious activities and connect the CNS to the skin and skeletal muscles. Autonomic nerve fibers of these nerves are involved in unconscious activities and connect the CNS to the visceral organs such as the heart, lungs, stomach, liver, pancreas, spleen, and intestines. Accordingly, to provide vagus nerve stimulation, an electrical signal may be applied to the patient's vagus nerve unilaterally or bilaterally, i.e., to one or both the branches of the vagus nerve. For example, coupling the electrodes 140(1-n) comprises coupling an electrode to at least one cranial nerve selected from the group consisting of the left vagus nerve and the right vagus nerve. The term "coupling" may include actual fixation, proximate location, and the like. The electrodes 140(1-n) may be coupled to a branch of the vagus nerve of the patient. The nerve branch 120 may be selected from the group consisting of the main trunk of the right or left vagus nerve, the esophageal plexus, the myenteric plexus of Auerbach, the submucosal plexus of Meissner, the principal nerve of the lesser curvature of the stomach, and the gastric branch.

Applying the electrical signal 115 to a selected autonomic nerve 105 may comprise generating a response selected from the group consisting of an afferent action potential, an efferent action potential, an afferent hyperpolarization, an efferent hyperpolarization, an afferent sub-threshold depolarization, and an efferent sub-threshold depolarization. The IMD 100 may generate an efferent action potential for treating an eating disorder.

The IMD 100 may comprise an electrical signal generator 150 and a controller 155 operatively coupled thereto to generate the electrical signal 115 for causing the nerve stimulation. The stimulus generator 150 may generate the electrical signal 115. The controller 155 may be adapted to apply the electrical signal 115 to the autonomic nerve 105 to provide electrical neurostimulation therapy to the patient for treating an eating disorder. The controller 155 may direct the stimulus generator 150 to generate the electrical signal 115 to stimulate the vagus nerve.

To generate the electrical signal 115, the IMD 100 may further include a battery 160, a memory 165, and a communication interface 170. More specifically, the battery 160 may comprise a power-source battery that may be rechargeable. The battery 160 provides power for the operation of the IMD 100, including electronic operations and the stimulation function. The battery 160, in one embodiment, may be a lithium/thionyl chloride cell or, in another embodiment, a lithium/carbon monofluoride cell. The memory 165, in one embodiment, is capable of storing various data, such as operation parameter data, status data, and the like, as well as program code. The communication interface 170 is capable of providing transmission and reception of electronic signals to and from an external unit, for example, by telemetry or wireless telecommunication. The external unit may be a device that is capable of programming the IMD 100.

The IMD 100, which may be a single device or a pair of devices, is implanted and electrically coupled to the lead(s) 135, which are in turn coupled to the electrode(s) 140 implanted on the left or right branches of the vagus nerve, for example. In one embodiment, the electrode(s) 140 (1-n) may include a set of stimulating electrode(s) separate from a set of sensing electrode(s). In another embodiment, the same electrode may be deployed to stimulate and to sense. A particular type or a combination of electrodes may be selected as desired for a given application. For example, an electrode suitable for coupling to a vagus nerve may be used. The electrodes 140 may comprise a bipolar stimulating electrode pair. Those skilled in the art having the benefit of the present invention will appreciate that many electrode designs could be used in the present invention.

Using the electrode(s) 140(1-n), the stimulus generator 150 may apply a predetermined sequence of electrical pulses to the selected autonomic nerve 105 to provide therapeutic neurostimulation for the patient with an eating disorder. While the selected autonomic nerve 105 may be the vagus nerve, the electrode(s) 140(1-n) may comprise at least one nerve electrode for implantation on the patient's vagus nerve for direct stimulation thereof. Alternatively, a nerve electrode may be implanted on or placed proximate to a branch of the patient's vagus nerve for direct stimulation thereof.

A particular embodiment of the IMD 100 may be a programmable electrical signal generator. Such a programmable electrical signal generator may be capable of programmablly defining the electrical signal 115. By using at least one parameter selected from the group consisting of a current magnitude, a pulse frequency, and a pulse width, the IMD 100 may treat an eating disorder. The IMD 100 may detect a symptom of the eating disorder. In response to detecting the symptom, the IMD 100 may initiate applying the electrical signal 115. For example, a sensor may be used to detect the symptom of an eating disorder. To treat the eating disorder, the IMD 100 may apply the electrical signal 115 during a first treatment period and further apply a second electrical signal to the autonomic nerve 105 using the electrode 140 during a second treatment period.

In one embodiment, the method may further include detecting a symptom of the eating disorder, wherein the applying the electrical signal 115 to the autonomic nerve 105 is initiated in response to the detecting of the symptom. In a further embodiment, the detecting the symptom may be performed by the patient. This may involve a subjective observation that the patient is experiencing a symptom of the eating disorder, such as an acid production factor, a muscle spasm relating to the diaphragm, a diaphragm measurement, spasms related to the esophagus, spasms related to the stomach region, an external input from the patient relating to nausea. Alternatively, or in addition, the symptom may be detected by performing an eating disorder test on the patient. Physiological responses can be detected by measuring smooth muscle contractility associated with an eating disorder such as, for example, using an electrogastrogram (EGG). This can be performed by sensing gastric myoelectric activity of the abdomen. Sensors can be implanted internally or may be located external on the surface of the abdomen.

The method may be performed under a single treatment regimen or under multiple treatment regimens. "Treatment regimen" herein may refer to a parameter of the electrical signal 115, duration for applying the signal, or a duty cycle of the signal, among others. In one embodiment, applying the electrical signal 115 to the autonomic nerve 105 is performed during a first treatment period, and may further include the step of applying a second electrical signal to the cranial nerve using the electrode 140 during a second treatment period. In a further embodiment, the method may include detecting a symptom of the pancreatic disorder, wherein the second treatment period is initiated upon the detection of the symptom. The patient may benefit by receiving a first electrical signal during a first, chronic treatment period and a second electrical signal during a second, acute treatment period. Three or more treatment periods may be used, if deemed desirable by a medical practitioner.

Figure 2:
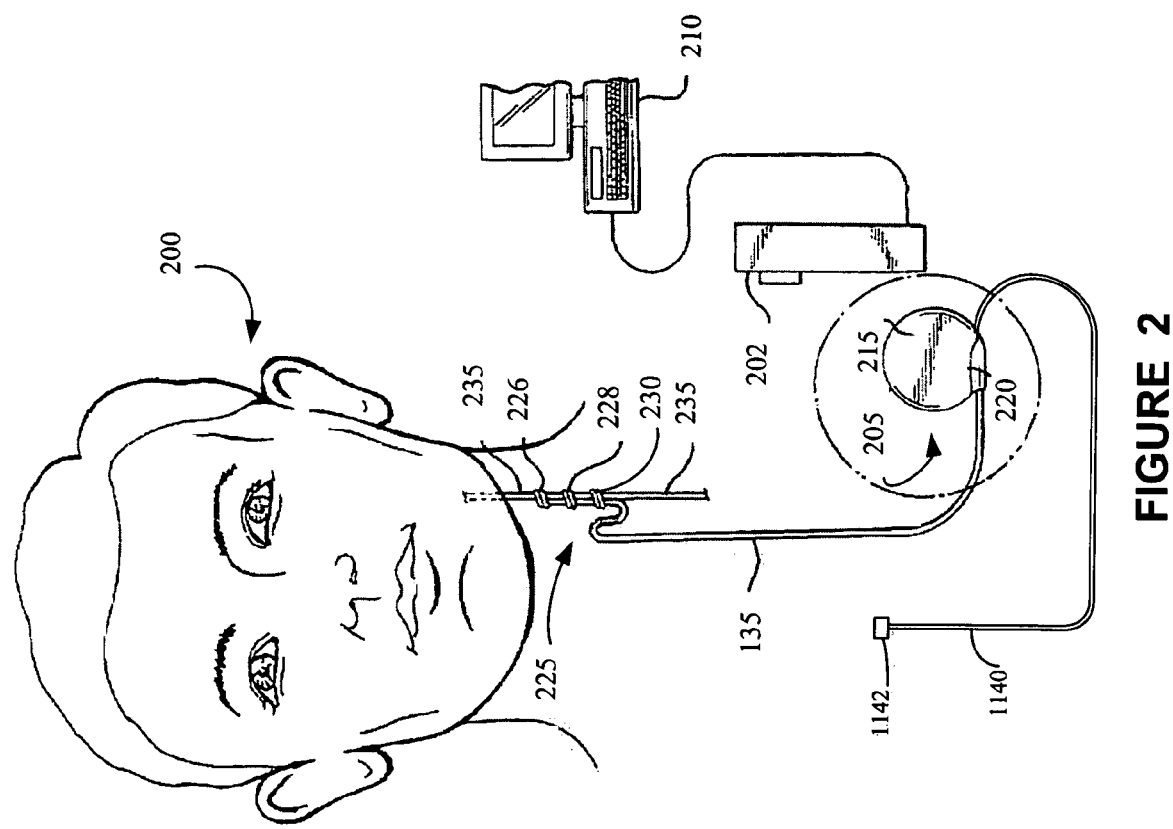
FIG. 2 illustrates one embodiment of a neurostimulator implanted into a patient's body for stimulating the vagus nerve of the patient, with an external programming user interface, in accordance with an illustrative embodiment of the present invention.

Turning now to FIG. 2, a particular embodiment of the IMD 100 shown in FIG. 1, in accordance with one illustrative embodiment of the present invention is provided. As shown therein, an electrode assembly 225, which may comprise a plurality of electrodes such as electrodes 226, 228, may be coupled to the autonomic nerve 105 such as vagus nerve 235 in accordance with an illustrative embodiment of the present invention. The lead 135 is coupled to the electrode assembly 225 and secured, while retaining the ability to flex with movement of the chest and neck. The lead 135 may be secured by a suture connection to nearby tissue. The electrode assembly 225 may deliver the electrical signal 115 to the autonomic nerve 105 to cause desired nerve stimulation for treating an eating disorder. Using the electrode(s) 226, 228, the selected cranial nerve such as vagus nerve 235, may be stimulated within a patient's body 200.

Although FIG. 2 illustrates a system for stimulating the left vagus nerve 235 in the neck (cervical) area, those skilled in the art having the benefit of the present disclosure will understand the electrical signal 105 for nerve stimulation may be applied to the right cervical vagus nerve in addition to, or instead of, the left vagus nerve, or to any autonomic nerve and remain within the scope of the present invention. In one such embodiment, lead 135 and electrode 225 assemblies substantially as discussed above may be coupled to the same or a different electrical signal generator.

An external programming user interface 202 may be used by a health professional for a particular patient to either initially program or to later reprogram the IMD 100, such as a neurostimulator 205. The neurostimulator 205 may include the electrical signal generator 150, which may be programmable. To enable physician-programming of the electrical and timing parameters of a sequence of electrical impulses, an external programming system 210 may include a processor-based computing device, such as a computer, personal digital assistant (PDA) device, or other suitable computing device.

Using the external programming user interface 202, a user of the external programming system 210 may program the neurostimulator 205. Communications between the neurostimulator 205 and the external programming system 210 may be accomplished using any of a variety of conventional techniques known in the art. The neurostimulator 205 may include a transceiver (such as a coil) that permits signals to be communicated wirelessly between the external programming user interface 202, such as a wand, and the neurostimulator 205.

The neurostimulator 205 having a case 215 with an electrically conducting connector on header 220 may be implanted in the patient's chest in a pocket or cavity formed by the implanting surgeon just below the skin, much as a pacemaker pulse generator would be implanted, for example. A stimulating nerve electrode assembly 225, preferably comprising an electrode pair, is conductively connected to the distal end of an insulated electrically conductive lead assembly 135, which preferably comprises a pair of lead wires and is attached at its proximal end to the connector on the case 215. The electrode assembly 225 is surgically coupled to a vagus nerve 235 in the patient's neck. The electrode assembly 225 preferably comprises a bipolar stimulating electrode pair 226, 228, such as the electrode pair described in U.S. Pat. No. 4,573,481 issued Mar. 4, 1986 to Bullara, which is hereby incorporated by reference herein in its entirety. One exemplary electrode assembly is available from Cyberonics, Inc., Houston, Tex. as the model 302 electrode assembly. Persons of skill in the art will appreciate that many electrode designs could be used in the present invention. The two electrodes 226, 228 are preferably wrapped about the vagus nerve, and the electrode assembly 225 secured to the nerve 235 by a spiral anchoring tether 230 such as that disclosed in U.S. Pat. No. 4,979,511 issued Dec. 25, 1990 to Reese S. Terry, Jr. and assigned to the same assignee as the instant application.

In one embodiment, the open helical design of the electrode assembly 225 (described in detail in the above-cited Bullara patent), which is self-sizing and flexible, minimizes mechanical trauma to the nerve and allows body fluid interchange with the nerve. The electrode assembly 225 conforms to the shape of the nerve, providing a low stimulation threshold by allowing a large stimulation contact area. Structurally, the electrode assembly 225 comprises two electrode ribbons (not shown), of a conductive material such as platinum, iridium, platinum-iridium alloys, or oxides of the foregoing. The electrode ribbons are individually bonded to an inside surface of an elastomeric body portion of two spiral electrodes, which may comprise two spiral loops of a three-loop helical assembly.

In one embodiment, the lead assembly 230 may comprise two distinct lead wires or a coaxial cable whose two conductive elements are respectively coupled to one of the conductive electrode ribbons. One suitable method of coupling the lead wires or cable to the electrodes comprises a spacer assembly such as that depicted in U.S. Pat. No. 5,531,778 issued Jul. 2, 1996, to Steven Maschino, et al. and assigned to the same Assignee as the instant application, although other known coupling techniques may be used. The elastomeric body portion of each loop is preferably composed of silicone rubber, and the third loop acts as the anchoring tether for the electrode assembly 225.

In one embodiment, the electrode(s) 140 (1-n) of IMD 100 (FIG. 1) may sense or detect any target symptom parameter in the patient's body 200. For example, an electrode 140 coupled to the patient's vagus nerve may detect a factor associated with an eating function. The electrode(s) 140 (1-n) may sense or detect an eating disorder condition. For example, a sensor or any other element capable of providing a sensing signal representative of a patient's body parameter associated with activity of the eating functions may be deployed.

The electrode(s) 140(1-n), as shown in FIG. 1 may be used in some embodiments of the invention to trigger administration of the electrical stimulation therapy to the vagus nerve 235 via electrode assembly 225. Use of such sensed body signals to trigger or initiate stimulation therapy is hereinafter referred to as "active," "triggered," or "feedback" modes of administration. Other embodiments of the present invention utilize a continuous, periodic or intermittent stimulus signal. These signals may be applied to the vagus nerve (each of which constitutes a form of continual application of the signal) according to a programmed on/off duty cycle. Sensors need not be used to trigger therapy delivery. This type of delivery may be referred to as a "passive" or "prophylactic" therapy mode. Both active and passive electrical biasing signals may be combined or delivered by a single neurostimulator according to the present invention.

The electrical signal generator 150 may be programmed using programming software of the type copyrighted by the assignee of the instant application with the Register of Copyrights, Library of Congress, or other suitable software based on the description herein. A programming wand (not shown) may be used to facilitate radio frequency (RF) communication between the external programming user interface 202 and the electrical signal generator 150. The wand and software permit noninvasive communication with the electrical signal generator 150 after the neurostimulator 205 is implanted. The wand may be powered by internal batteries, and provided with a "power on" light to indicate sufficient power for communication. Another indicator light may be provided to show that data transmission is occurring between the wand and the neurostimulator 205.

The neurostimulator 205 may provide vagus nerve stimulation therapy upon a vagus nerve branch or to any portion of the autonomic nervous system. The neurostimulator 205 may be activated manually or automatically to deliver the electrical bias signal to the selected cranial nerve via the electrode(s) 226, 228. The neurostimulator 205 may be programmed to deliver the electrical signal 105 continuously, periodically or intermittently when activated.

In one embodiment, a sensory stimulation lead 240 may be coupled to the neurostimulator 205. The sensory stimulation lead 240 may deliver an electrical signal to a sensory stimulation device 242 implanted at a suitable location in the body. Determining a suitable location is a matter of routine experimentation for the ordinary skilled artisan having the benefit of the present disclosure. The sensory stimulation device 242 may convert the electrical signal to a noxious stimulus, a pain stimulus, or a temperature stimulus, a discomfort stimulation, among others.

In another embodiment, a single lead can perform the functions of both the sensory stimulation lead 240 and the electrode 140. A single device can perform the functions of both the sensory stimulation device 242 and the electrode assembly 225. In this embodiment, a separate sensory stimulation device/circuit is not required. Stimulation of the nerve can cause an evoked potential in the brain that is detectable by EEG sensors and equipment.

Figure 3A:
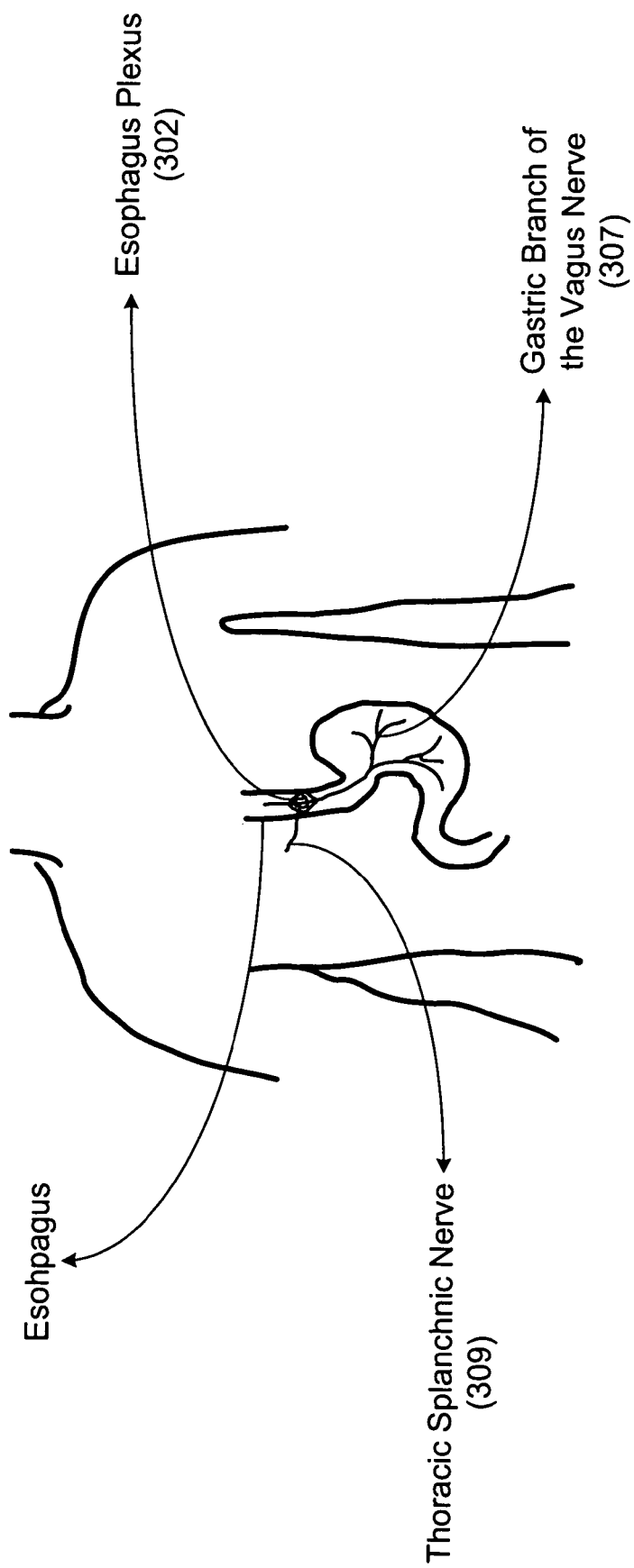
FIG. 3A illustrates a stylized diagram of the esophagus, stomach, and the vagus nerve innervating the esophagus and the stomach regions.

Turning now to FIGS. 3A, 3B, 3C and 3D, various stylized depiction of the esophagus and the stomach regions of a human body are illustrated. FIG. 3A illustrates a stylized diagram of the esophagus, stomach, and the vagus nerve innervating the esophagus and the stomach regions. In order to treat an eating disorder, the IMD 100 may be used to stimulate a portion of the vagus nerve, such as the esophageal plexus, the myenteric plexus of Auerbach, the submucosal plexus of Meissner, or other portions of the gastric branches of the vagus nerve. Additionally, stimulation of the left vagus main trunk or the right vagus main trunk may be performed to treat an eating disorder. The diagrams illustrated in FIGS. 3A-3D have been simplified for ease and clarity of description, however, those skilled in the art would appreciate that various details have been simplified for the sake of clarity.

Referring simultaneously to FIGS. 3A-3D, the vagus nerve descends below the lung root and diverges into two to four parts, which become relatively opposed to the esophagus while descending. Descending down the esophagus, the vagus nerve divides and reunites to form an open meshed nerve region called the esophageal plexus 302, containing small ganglia. The right vagus nerve portions incline posteriorly, while most of the left vagus nerve portions incline anteriorly. The esophageal plexus 302 includes components of the sympathetic trunks as well as the parasympathetic vagus components. The sympathetic nerve components include at least portions of the thoracic splanchnic nerve 309.

The nerves involved in the esophageal plexus 302 contain efferent and afferent, sympathetic and parasympathetic fibers derived from various sympathetic trunks, such as the splanchnic nerve, and the vagus nerve. The myenteric plexus of Auerbach 350 is generally relatively a coarse type nerve system, with a thicker mesh and larger ganglia. The main or primary meshes of the myenteric plexus of Auerbach 350 give off fascicles that form secondary networks in the interstices of the primary network. These fascicles then generally spread into bundles of fibers that ramify between the muscle tunics to supply them.

The submucosal plexus of Meissner 360 is more delicate than the nerves associated with the myenteric plexus of Auerbach 350. The myenteric plexus 350 and the submucosal plexus 360 generally become more defined near the esophagus as they approach the stomach. The ganglia are not uniformly distributed. The ganglion cells are less dense near the esophagus. Various interconnections exist between the myenteric plexus 350 and the submucosal plexus 360. The myenteric plexus 350 generally innervates the muscle layers in the visceral walls. The submucosal plexus 360 generally innervates the glands and muscularis mucosa. In this region, the sympathetic innervations are primarily inhibitory, while the parasympathetic innervations are generally opposite.

Figure 3B:
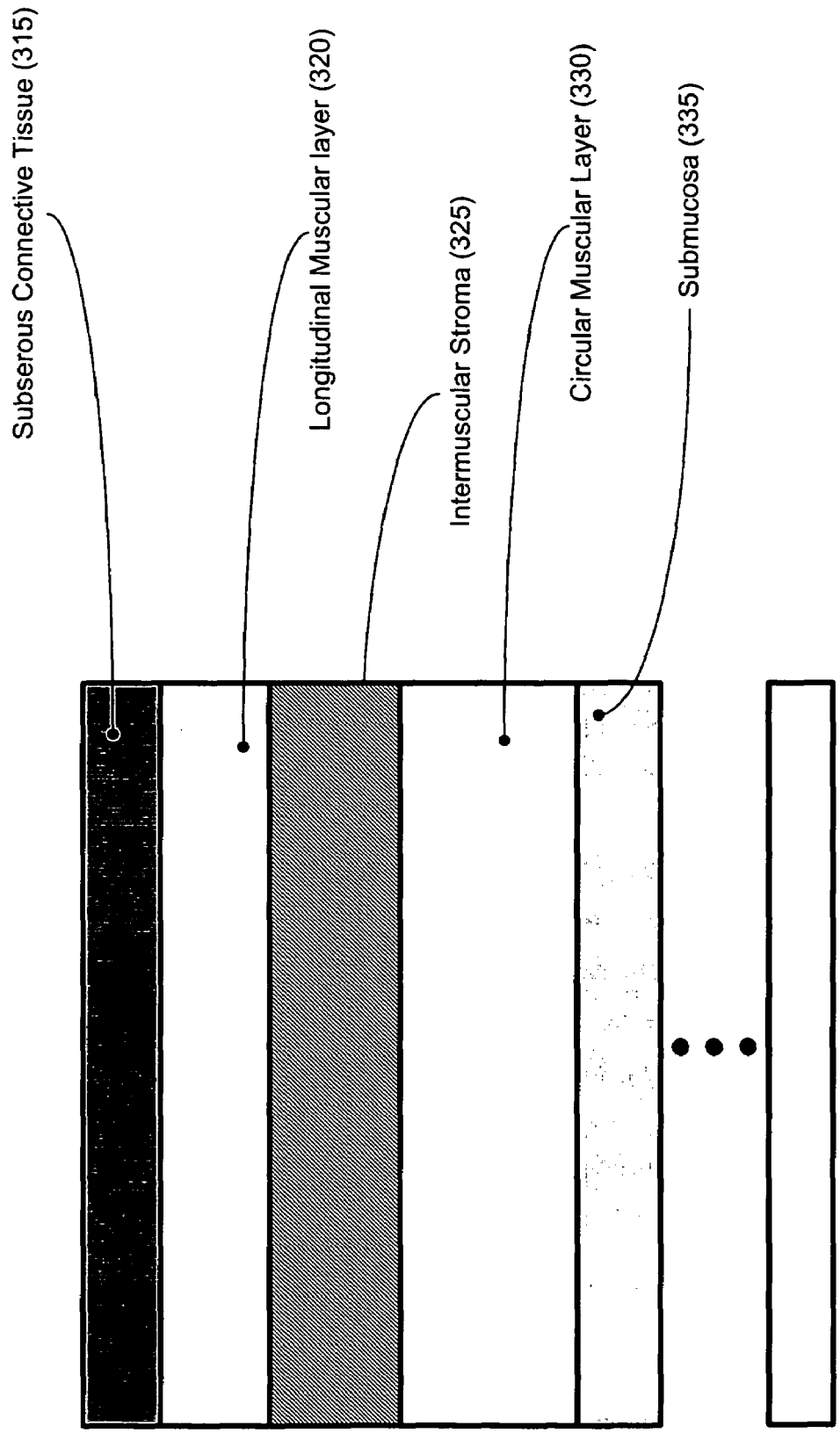
FIG. 3B depicts a stylized diagram of a cross-sectional view of the esophagus region.

Embodiments of the present invention provide for stimulating portions of the esophageal plexus 302, as well as other portions of the gastric branch 307. As illustrated in FIG. 3B, a cross-sectional view of a portion of the layers of the esophagus is illustrated. The layers include a visceral peritoneum 310, which resides over the subserous connective tissue 315. Below this layer is the longitudinal muscular layer 320, followed by the intermuscular stoma 325. Below the intramuscular stoma 325 is the circular muscular layer 330, followed by the submucosa 335. As illustrated in FIG. 3C, the intermuscular stoma layer 325 includes the myenteric plexus of Auerbach 350. The myenteric plexus of Auerbach 350 is a portion emerging from the gastric branches 307 of the vagus nerve. Those skilled in the art would appreciate that some of the layers have been omitted from FIG. 3B in the interest of clarity and conciseness.

Figure 3D:
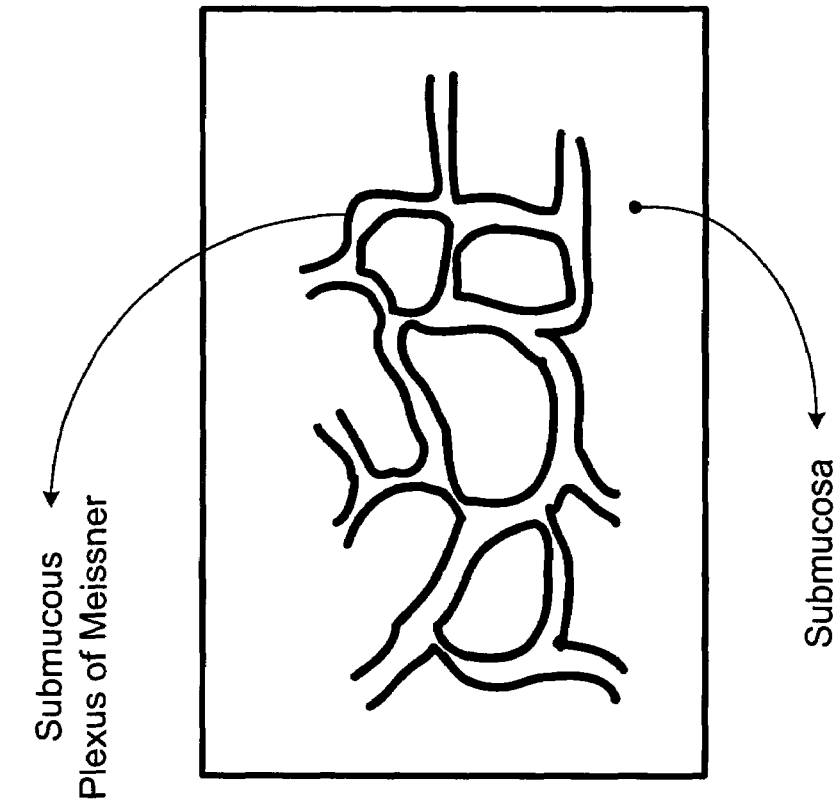
FIG. 3D depicts a stylized diagram of the submucosal plexus of Meissner in the submucosa of the esophagus region.
Figure 3C:
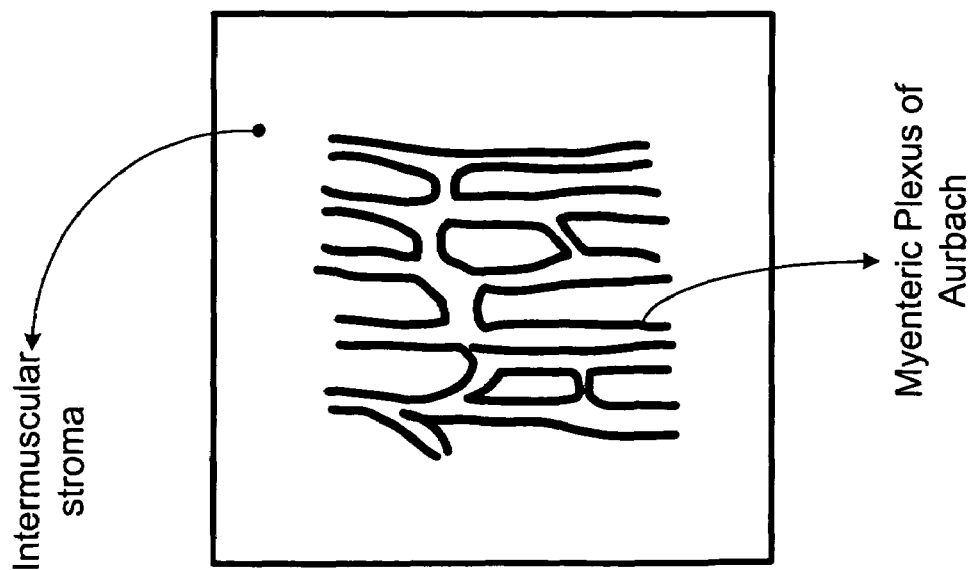
FIG. 3C depicts a stylized diagram of the Myenteric plexus of Auerbach in the intermuscular stroma in the esophagus region.

FIG. 3D illustrates the submucosa layer 335, which includes a submucosal plexus of Meissner 360. The submucosal plexus of Meissner 360 is also formed from the gastric branches 307 of the vagus nerve. Embodiments of the present invention provides for positioning electrodes, such that they are operatively coupled to the one or more of the esophageal plexus 302, the myenteric plexus of Auerbach 350, the submucosal plexus of Meissner 360, or other portions of the gastric branches 307 of the vagus nerve.

The "operatively coupled" feature may include actual contact of the electrode to portions of the nerves described above. The term "operatively coupled" may also include sufficient proximity of the placement of the electrodes to the nerve portions, such that an electrical signal sent to the electrode is capable of stimulating various portions of the vagus nerve described herein. Stimulation of the myenteric plexus of Auerbach 350, the esophagus plexus 302, or the submucosal plexus of Meissner 360 may be performed to treat and improve conditions relating to eating disorders, such as anorexia nervosa, bulimia nervosa, compulsive eating, binge eating disorders, etc.

In one embodiment, stimulation may be applied in an efferent manner which refers to signals being traveling on a nerve in a direction away from the central nervous system. Therefore, a "blocking" type of stimulation may be employed using the IMD 100, such that afferent fibers are not stimulated, or efferent fibers are stimulated. Therefore, an appreciable amount of blockage of signals sent back to the brain via the vagus nerve is achieved on employing efferent type of stimulation to affect the operation of portions of the body proximate to the esophagus or the stomach. Additionally, the principal nerve of the lesser curvature of the stomach, originating from the gastric branch of the vagus nerve may be stimulated to treat the various eating disorders described herein.

Further, afferent stimulation may also be performed, wherein afferent fibers are stimulated while efferent fibers are not stimulated or are blocked. Various eating disorders, such as bulimia nervosa, anorexia nervosa, binge eating disorders, compulsive eating disorders, etc., may be treated by performing afferent stimulation of the vagus nerve via the regions proximate to the gastric branches 307 of the vagus nerve. In addition to efferent or afferent fiber stimulation, additional stimulation may be provided in combination with the blocking type of stimulation described above. Efferent blocking may be realized by enhancing the hyper polarization of a stimulation signal, as described below. Embodiments of the present invention may employ the IMD 100 to perform stimulation in combination with signal blocking, in order to treat eating disorders. Using the stimulation from the IMD 100, parasympathetic nerve portions may be inhibited such that blocking of stimulation is achieved, wherein the various portions of the parasympathetic nerve may also be stimulated to affect a gastrointestinal mechanism in the patients' body. In this way, afferent as well as efferent stimulation may be performed by the IMD 100 to treat various eating disorders.

The electrical stimulation treatment described herein may be used to treat eating disorders separately, or in combination with another type of treatment. For example, electrical stimulation treatment may be applied in combination with a chemical agent, such as various drugs, to treat various disorders relating to the gastrointestinal system. Therefore, various drugs may be taken by a patient, wherein the effects of these drugs may be enhanced by providing electrical stimulation to various portions of the nerves described herein to treat pancreas-related disorders, such as diabetes. Further, the electrical stimulation may be performed in combination with treatment(s) relating to a biological agent, such as hormones. Therefore, hormone therapy may be enhanced by the application of the stimulation provided by the IMD 100. The electrical stimulation treatment may also be performed in combination with other types of treatment, such as magnetic stimulation treatment or biological treatments. Combining the electrical stimulation with the chemical, magnetic, or biological treatments, side effects associated with certain drugs or biological agents may be reduced.

In addition to efferent fiber stimulation, additional stimulation may be provided in combination with the blocking type of stimulation described above. Efferent blocking may be realized by enhancing the hyperpolarization of a stimulation signal, as described below. Embodiments of the present invention may be employed to cause the IND 100 to perform stimulation in combination with signal blocking, in order to treat eating disorders. Using stimulation from the IMD 100, parasympathetic nerve portions are be inhibited such that stimulation blocking is achieved, wherein the various portions of the parasympathetic nerve may also be stimulated to affect a gastrointestinal mechanism in a patient's body. In this way, afferent as well as efferent stimulation may be performed by the IMD 100 to treat various eating disorders.

Figure 4A:
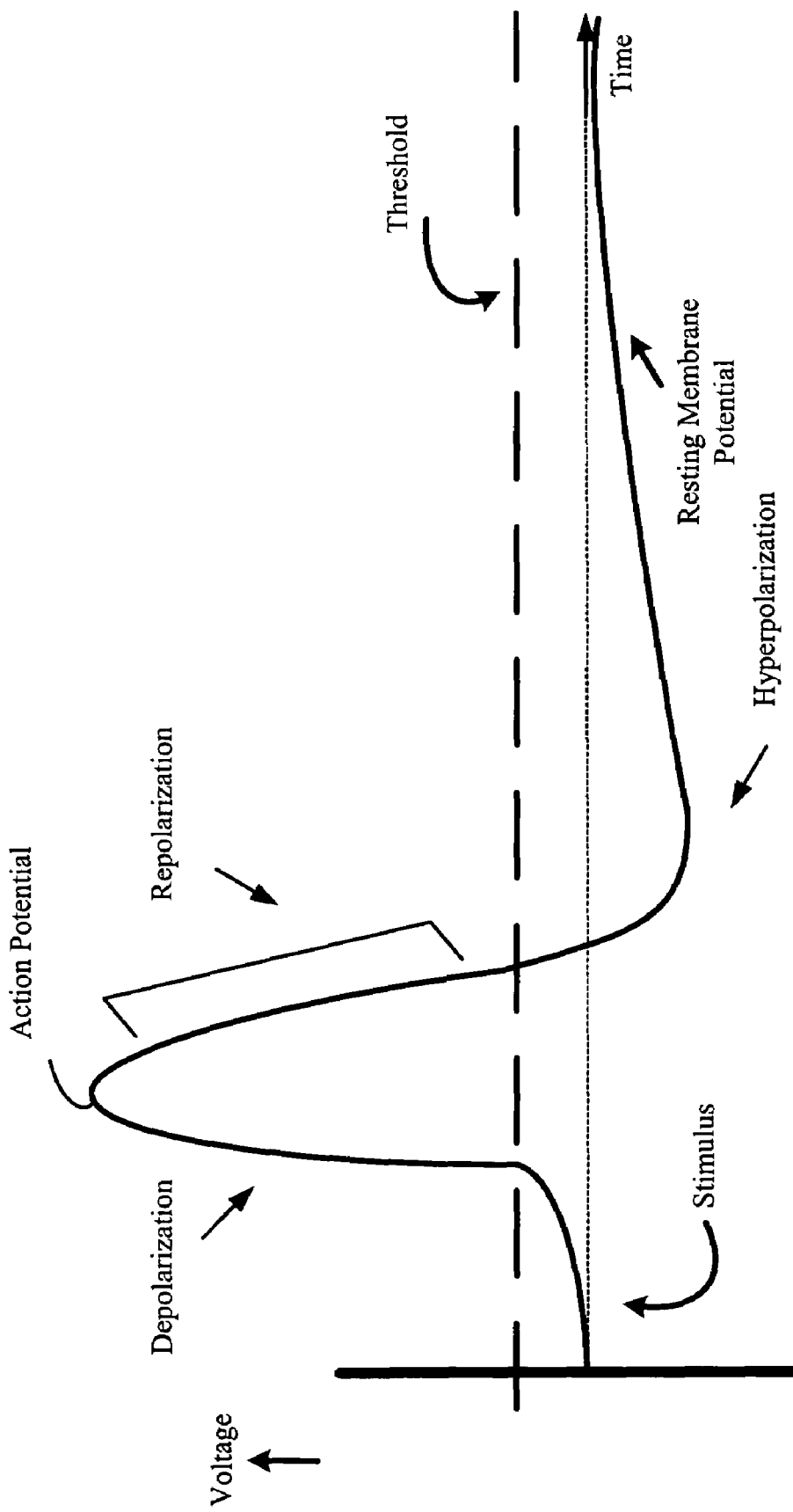
FIG. 4A illustrates an exemplary electrical signal of a firing neuron as a graph of voltage at a given location at particular times during firing by the neurostimulator of FIG. 2, when applying an electrical signal to the autonomic nerves, in accordance with one illustrative embodiment of the present invention.

FIG. 4A provides a stylized depiction of an exemplary electrical signal of a firing neuron as a graph of voltage at a given location at particular times during firing, in accordance with one embodiment of the present invention. A typical neuron has a resting membrane potential of about −70 mV, maintained by transmembrane ion channel proteins. When a portion of the neuron reaches a firing threshold of about −55 mV, the ion channel proteins in the locality allow the rapid ingress of extracellular sodium ions, which depolarizes the membrane to about +30 mV. The wave of depolarization then propagates along the neuron. After depolarization at a given location, potassium ion channels open to allow intracellular potassium ions to exit the cell, lowering the membrane potential to about −80 mV (hyperpolarization). About 1 msec is required for transmembrane proteins to return sodium and potassium ions to their starting intra- and extracellular concentrations and allow a subsequent action potential to occur. The present invention may raise or lower the resting membrane potential, thus making the reaching of the firing threshold more or less likely and subsequently increasing or decreasing the rate of fire of any particular neuron.

Referring to FIG. 4B, an exemplary electrical signal response is illustrated of a firing neuron as a graph of voltage at a given location at particular times during firing by the neurostimulator of FIG. 2, in accordance with one illustrative embodiment of the present invention. As shown in FIG. 4C, an exemplary stimulus including a sub-threshold depolarizing pulse and additional stimulus to the cranial nerve 105, such as the vagus nerve 235, may be applied for firing a neuron, in accordance with one illustrative embodiment of the present invention. The stimulus illustrated in FIG. 4C depicts a graph of voltage at a given location at particular times by the neurostimulator of FIG. 2.

The neurostimulator may apply the stimulus voltage of FIG. 4C to the autonomic nerve 105, which may include afferent fibers, efferent fibers, or both. This stimulus voltage may cause the response voltage shown in FIG. 4B. Afferent fibers transmit information to the brain from the extremities; efferent fibers transmit information from the brain to the extremities. The vagus nerve 235 may include both afferent and efferent fibers, and the neurostimulator 205 may be used to stimulate either or both.

The autonomic nerve 105 may include fibers that transmit information in the sympathetic nervous system, the parasympathetic nervous system, or both. Inducing an action potential in the sympathetic nervous system may yield a result similar to that produced by blocking an action potential in the parasympathetic nervous system and vice versa.

Figures 5A, 5B:
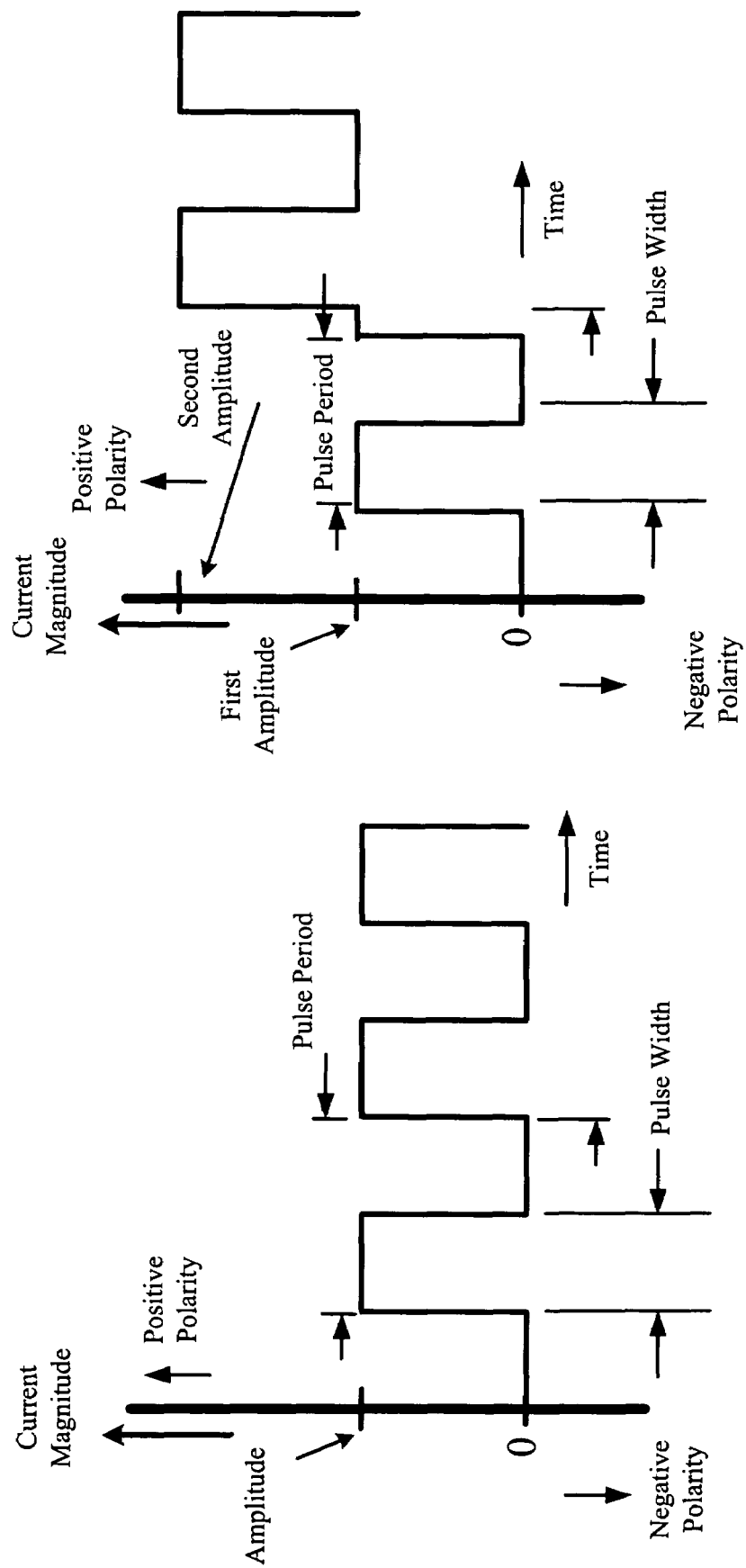
FIGS. 5A, 5B, and 5C illustrate exemplary waveforms for generating the electrical signals for stimulating the vagus nerve for treating an eating disorder, according to one illustrative embodiment of the present invention.
Figure 5C:
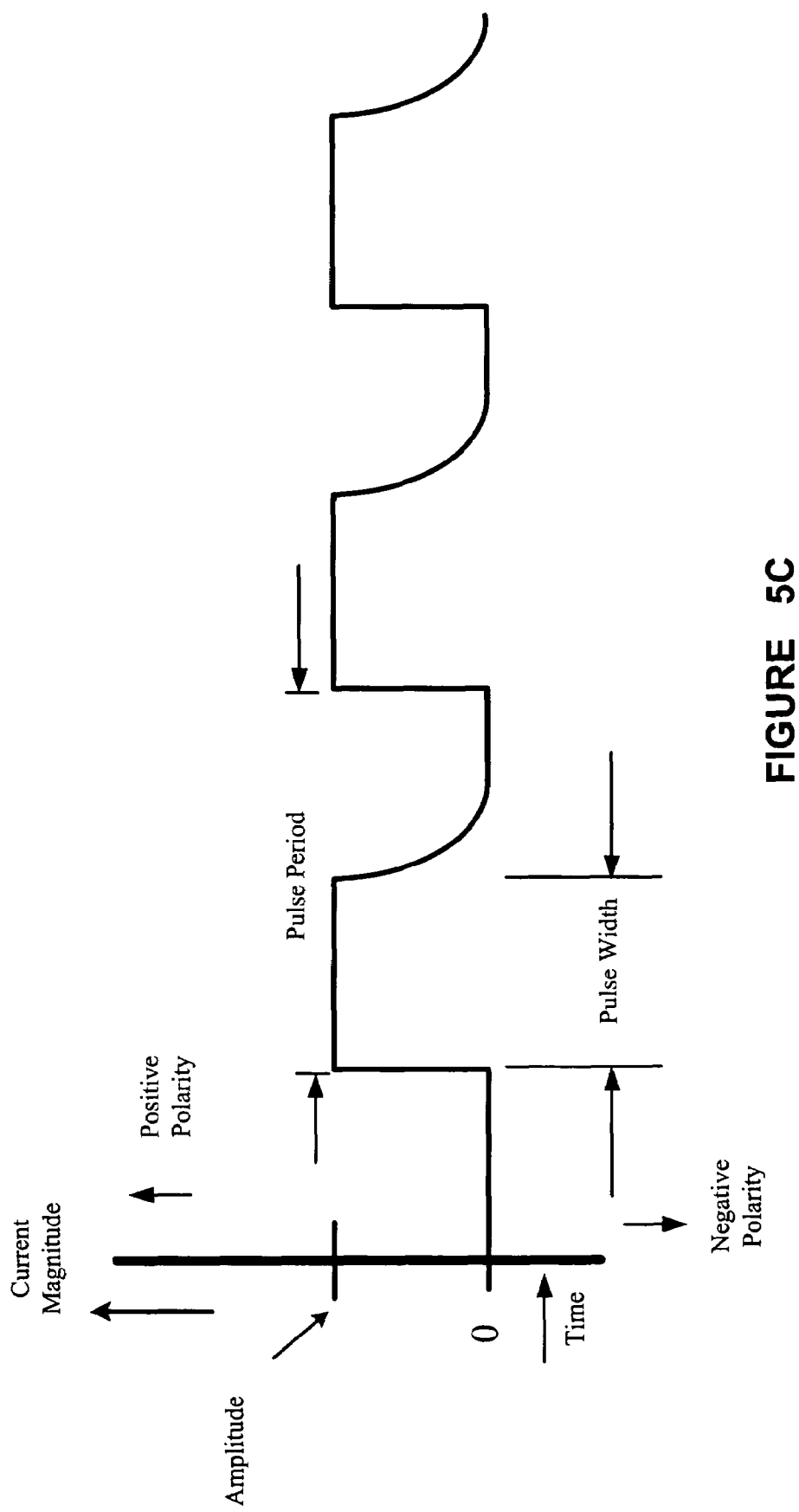

Referring back to FIG. 2, the neurostimulator 205 may generate the electrical signal 115 according to one or more programmed parameters for stimulation of the vagus nerve 235. In one embodiment, the stimulation parameter may be selected from the group consisting of a current magnitude, a pulse frequency, a pulse width, on-time, and off-time. An exemplary table of ranges for each of these stimulation parameters is provided in Table 1. The stimulation parameter may be of any suitable waveform; exemplary waveforms in accordance with one embodiment of the present invention are shown in FIGS. 5A-5C. Specifically, the exemplary waveforms illustrated in FIGS. 5A-5C depict the generation of the electrical signal 115 that may be defined by a factor related to at least one of an acid production, a muscle spasm relating to the diaphragm, a spasm related to an esophagus region, a spasm related to the stomach region, and a condition relating to at least one of a chronic nausea, a motility disorder, anorexia nervosa, bulimia nervosa, compulsive overeating, and binge overeating, relative to a value within a defined range.

According to one illustrative embodiment of the present invention, various electrical signal patterns may be employed by the neurostimulator 205. These electrical signals may include a plurality of types of pulses, e.g., pulses with varying amplitudes, polarity, frequency, etc. For example, the exemplary waveform 5A depicts that the electrical signal 115 may be defined by fixed amplitude, constant polarity, pulse width, and pulse period. The exemplary waveform 5B depicts that the electrical signal 115 may be defined by a variable amplitude, constant polarity, pulse width, and pulse period. The exemplary waveform 5C depicts that the electrical signal 115 may be defined by a fixed amplitude pulse with a relatively slowly discharging current magnitude, constant polarity, pulse width, and pulse period. Other types of signals may also be used, such as sinusoidal waveforms, etc. The electrical signal may be controlled current signals.

TABLE 1

| PARAMETER | RANGE |
| --- | --- |
| Output current | 0.1-6.0 mA |
| Pulse width | 10-1500 μsec |
| Frequency | 0.5-2500 Hz |
| On-time | 1 sec and greater |
| Off-time | 0 sec and greater |
| Frequency Sweep | 10-100 Hz |
| Random Frequency | 10-100 Hz |

On-time and off-time parameters may be used to define an intermittent pattern in which a repeating series of signals may be generated for stimulating the nerve 105 during the on-time. Such a sequence may be referred to as a "pulse burst." This sequence may be followed by a period in which no signals are generated. During this period, the nerve is allowed to recover from the stimulation during the pulse burst. The on/off duty cycle of these alternating periods of stimulation and idle periods may have a ratio in which the off-time may be set to zero, providing continuous stimulation. Alternatively, the idle time may be as long as one day or more, in which case the stimulation is provided once per day or at even longer intervals. Typically, however, the ratio of "off-time" to "on-time" may range from about 0.5 to about 10.

In one embodiment, the width of each signal may be set to a value not greater than about 1 msec, such as about 250-500 μsec, and the signal repetition frequency may be programmed to be in a range of about 20-2500 Hz. A non-uniform frequency may also be used. Frequency may be altered during a pulse burst by either a frequency sweep from a low frequency to a high frequency, or vice versa. Alternatively, the timing between adjacent individual signals within a burst may be randomly changed such that two adjacent signals may be generated at any frequency within a range of frequencies.

In one embodiment, the present invention may include coupling of at least one electrode to each of two or more cranial nerves. (In this context, two or more cranial nerves mean two or more nerves having different names or numerical designations, and do not refer to the left and right versions of a particular nerve). In one embodiment, at least one electrode 140 may be coupled to each of the vagus nerve 235 or a branch of the vagus nerve. The electrode 140 may be operatively coupled to the main trunk of the right vagus nerve, the main trunk of the left vagus nerve, the esophageal plexus 302, a myenteric plexus of Auerbach 350, a submucosal plexus of Meissner 360, a principal nerve of the lesser curvature of the stomach, and a gastric branch 307 of a vagus nerve. The term "operatively" coupled may include directly or indirectly coupling. Each of the nerves in this embodiment or others involving two or more cranial nerves may be stimulated according to particular activation modalities that may be independent between the two nerves.

Another activation modality for stimulation is to program the output of the neurostimulator 205 to the maximum amplitude which the patient may tolerate. The stimulation may be cycled on and off for a predetermined period of time followed by a relatively long interval without stimulation. Where the cranial nerve stimulation system is completely external to the patient's body, higher current amplitudes may be needed to overcome the attenuation resulting from the absence of direct contact with the vagus nerve 235 and the additional impedance of the skin of the patient. Although external systems typically require greater power consumption than implantable ones, they have an advantage in that their batteries may be replaced without surgery.

Other types of indirect stimulations may be performed in conjunction with embodiments of the invention. In one embodiment, the invention includes providing noninvasive transcranial magnetic stimulation (TMS) to the brain 125 of the patient along with the IMD 100 of the present information to treat the eating disorder. TMS systems include those disclosed in U.S. Pat. Nos. 5,769,778; 6,132,361; and 6,425,852. Where TMS is used, it may be used in conjunction with cranial nerve stimulation as an adjunctive therapy. In one embodiment, both TMS and direct cranial nerve stimulation may be performed to treat the eating disorder. Other types of stimulation, such as chemical stimulation to treat eating disorders may be performed in combination with the IMD 100.

Returning to systems for providing autonomic nerve stimulation, such as that shown in FIGS. 1 and 2, stimulation may be provided in at least two different modalities. Where cranial nerve stimulation is provided based solely on programmed off-times and on-times, the stimulation may be referred to as passive, inactive, or non-feedback stimulation. In contrast, stimulation may be triggered by one or more feedback loops according to changes in the body or mind of the patient. This stimulation may be referred to as active or feedback-loop stimulation. In one embodiment, feedback-loop stimulation may be manually-triggered stimulation, in which the patient manually causes the activation of a pulse burst outside of the programmed on-time/off-time cycle. The patient may manually activate the neurostimulator 205 to stimulate the autonomic nerve 105 to treat the acute episode of an eating disorder, such as an excessively high blood-glucose level. The patient may also be permitted to alter the intensity of the signals applied to the autonomic nerve within limits established by the physician. For example, the patient may be permitted to alter the signal frequency, current, duty cycle, or a combination thereof. In at least some embodiments, the neurostimulator 205 may be programmed to generate the stimulus for a relatively long period of time in response to manual activation.

Patient activation of a neurostimulator 205 may involve use of an external control magnet for operating a reed switch in an implanted device, for example. Certain other techniques of manual and automatic activation of implantable medical devices are disclosed in U.S. Pat. No. 5,304,206 to Baker, Jr., et al., assigned to the same assignee as the present application ("the '206 patent"). According to the '206 patent, means for manually activating or deactivating the electrical signal generator 150 may include a sensor such as piezoelectric element mounted to the inner surface of the generator case and adapted to detect light taps by the patient on the implant site. One or more taps applied in fast sequence to the skin above the location of the electrical signal generator 150 in the patient's body 200 may be programmed into the implanted medical device 100 as a signal for activation of the electrical signal generator 150. Two taps spaced apart by a slightly longer duration of time may be programmed into the IMD 100 to indicate a desire to deactivate the electrical signal generator 150, for example. The patient may be given limited control over operation of the device to an extent which may be determined by the program dictated or entered by the attending physician. The patient may also activate the neurostimulator 205 using other suitable techniques or apparatus.

In some embodiments, feedback stimulation systems other than manually-initiated stimulation may be used in the present invention. An autonomic nerve stimulation system may include a sensing lead coupled at its proximal end to a header along with a stimulation lead and electrode assemblies. A sensor may be coupled to the distal end of the sensing lead. The sensor may include a temperature sensor, a gastrointestinal parameter sensor, a heart parameter sensor, a brain parameter sensor, or a sensor for another body parameter. The sensor may also include a nerve sensor for sensing activity on a nerve, such as a cranial nerve, such as the vagus nerve 235.

In one embodiment, the sensor may sense a body parameter that corresponds to a symptom of an eating disorder. If the sensor is to be used to detect a symptom of the eating disorder, a signal analysis circuit may be incorporated into the neurostimulator 205 for processing and analyzing signals from the sensor. Upon detection of the symptom of the eating disorder, the processed digital signal may be supplied to a microprocessor in the neurostimulator 205 to trigger application of the electrical signal 115 to the autonomic nerve 105. In another embodiment, the detection of a symptom of interest may trigger a stimulation program including different stimulation parameters from a passive stimulation program. This may entail providing a higher current stimulation signal or providing a higher ratio of on-time to off-time.

In response to the afferent action potentials, the detection communicator may detect an indication of change in the symptom characteristic. The detection communicator may provide feedback for the indication of change in the symptom characteristic to modulate the electrical signal 115. In response to providing feedback for the indication, the electrical signal generator 150 may adjust the afferent action potentials to enhance efficacy of a drug in the patient.

The neurostimulator 205 may use the memory 165 to store disorder data and a routine to analyze this data. The disorder data may include sensed body parameters or signals indicative of the sensed parameters. The routine may comprise software or firmware instructions to analyze the sensed hormonal activity for determining whether electrical neurostimulation would be desirable. If the routine determines that electrical neurostimulation is desired, then the neurostimulator 205 may provide an appropriate electrical signal to a neural structure, such as the vagus nerve 235.

In certain embodiments, the IMD 100 may comprise a neurostimulator 205 having a case 215 as a main body in which the electronics described in FIGS. 1-2 may be enclosed and hermetically sealed. Coupled to the main body may be the header 220 designed with terminal connectors for connecting to a proximal end of the electrically conductive lead(s) 135. The main body may comprise a titanium shell, and the header may comprise a clear acrylic or other hard, biocompatible polymer such as polycarbonate, or any material that may be implantable into a human body. The lead(s) 135 projecting from the electrically conductive lead assembly 230 of the header may be coupled at a distal end to electrodes 140(1-n). The electrodes 140(1-n) may be coupled to neural structure such as the vagus nerve 235, using a variety of methods for operatively coupling the lead(s) 135 to the tissue of the vagus nerve 235. Therefore, the current flow may take place from one terminal of the lead 135 to an electrode such as electrode 226 (FIG. 2) through the tissue proximal to the vagus nerve 235, to a second electrode such as electrode 228 and a second terminal of the lead 135.

Figure 6:
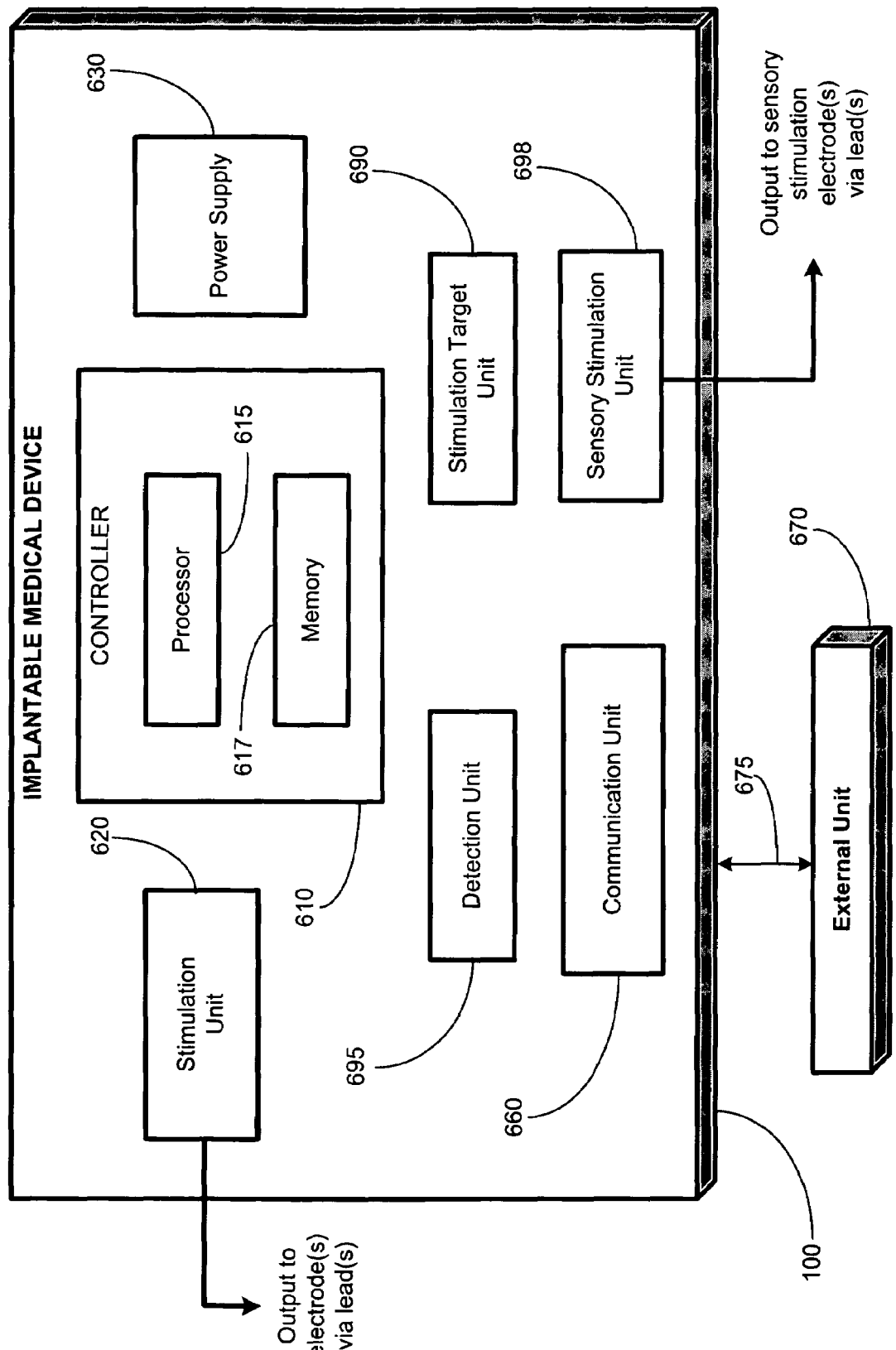
FIG. 6 illustrates a stylized block diagram depiction of the implantable medical device for treating an eating disorder, in accordance with one illustrative embodiment of the present invention.

Turning now to FIG. 6, a block diagram depiction of the IMD 100, in accordance with an illustrative embodiment of the present invention is provided. The IMD 100 may comprise a controller 610 capable of controlling various aspects of the operation of the IMD 100. The controller 610 is capable of receiving internal data or external data and generating and delivering a stimulation signal to target tissues of the patient's body. For example, the controller 610 may receive manual instructions from an operator externally, or may perform stimulation based on internal calculations and programming. The controller 610 is capable of affecting substantially all functions of the IMD 100.

The controller 610 may comprise various components, such as a processor 615, a memory 617, etc. The processor 615 may comprise one or more microcontrollers, microprocessors, etc., that are capable of performing various executions of software components. The memory 617 may comprise various memory portions where a number of types of data (e.g., internal data, external data instructions, software codes, status data, diagnostic data, etc.) may be stored. The memory 617 may comprise random access memory (RAM) dynamic random access memory (DRAM), electrically erasable programmable read-only memory (EEPROM), flash memory, etc.

The IMD 100 may also comprise a stimulation unit 620. The stimulation unit 620 is capable of generating and delivering stimulation signals to one or more electrodes via leads. A number of leads 122, 134, 137 may be coupled to the IMD 100. Therapy may be delivered to the leads 122 by the stimulation unit 620 based upon instructions from the controller 610. The stimulation unit 620 may comprise various circuitry, such as stimulation signal generators, impedance control circuitry to control the impedance "seen" by the leads, and other circuitry that receives instructions relating to the type of stimulation to be performed. The stimulation unit 620 is capable of delivering a controlled current stimulation signal over the leads 122. In addition to delivering a stimulation signal, the stimulation unit 620 is also capable of delivering a sensory stimulus signal to the patient. The sensory stimulus signal may include a pain stimulus, a noxious stimulus, temperature stimulus, and/or any type of sensory stimulus.

The IMD 100 may also comprise a power supply 630. The power supply 630 may comprise a battery, voltage regulators, capacitors, etc., to provide power for the operation of the IMD 100, including delivering the stimulation signal. The power supply 630 comprises a power-source battery that in some embodiments may be rechargeable. In other embodiments, a non-rechargeable battery may be used. The power supply 630 provides power for the operation of the IMD 100, including electronic operations and the stimulation function. The power supply 630 may comprise a lithium/thionyl chloride cell or a lithium/carbon monofluoride cell. Other battery types known in the art of implantable medical devices may also be used.

The IMD 100 also comprises a communication unit 660 capable of facilitating communications between the IMD 100 and various devices. In particular, the communication unit 660 is capable of providing transmission and reception of electronic signals to and from an external unit 670. The external unit 670 may be a device that is capable of programming various modules and stimulation parameters of the IMD 100. In one embodiment, the external unit 670 is a computer system that is capable of executing a data-acquisition program. The external unit 670 may be controlled by a healthcare provider, such as a physician, at a base station in, for example, a doctor's office. The external unit 670 may be a computer, preferably a handheld computer or PDA, but may alternatively comprise any other device that is capable of electronic communications and programming. The external unit 670 may download various parameters and program software into the IMD 100 for programming the operation of the implantable device. The external unit 670 may also receive and upload various status conditions and other data from the IMD 100. The communication unit 660 may be hardware, software, firmware, or any combination thereof. Communications between the external unit 670 and the communication unit 660 may occur via a wireless or other type of communication, illustrated generally by line 675 in FIG. 6.

The IMD 100 also comprises a detection unit 695 that is capable of detecting various conditions and characteristics of the eating function(s) of a patient. For example, the detection unit 695 may comprise hardware, software, or firmware that are capable of determining data relating to an acid production factor, muscle spasm relating to the diaphragm, diaphragm measurements, spasms related to the esophagus or the stomach region, external input from the patient relating to nausea or other eating disorders, etc. The detection unit 695 may comprise means for deciphering data from various sensors that are capable of measuring the factors described herein. Based upon the data deciphered by the detection unit 695, the IMD 100 may deliver stimulation to a portion of the autonomous nerve to affect the eating function(s) of the patient. In one embodiment, the detection unit 695 may be capable of detecting a feedback response from the patient. The feedback response may include a magnetic signal input, a tap input, etc. The feedback may be indicative of a pain and/or noxious threshold, wherein the threshold may be the limit of tolerance of discomfort for a particular patient.

The IMD 100 may also comprise a stimulation target unit 690 that is capable of directing a stimulation signal to one or more electrodes that is operationally coupled to various portions of the autonomous nerves. The stimulation target unit 690 may direct a stimulation signal to the esophageal plexus 302, myenteric plexus of Auerbach 350, the submucosal plexus of Meissner 360, the principal nerve of the lesser curvature of the stomach, the gastric branch 307, the left vagus main trunk, or the right vagus main trunk. In this way, the stimulation target unit is capable of targeting a predetermined portion of the eating region. Therefore, based upon a particular type of data detected by the detection unit 695, the stimulation target unit 690 may stimulate a selective portion of the eating system to perform an afferent, an efferent, or an afferent-efferent combination stimulation to treat an eating disorder. Therefore, upon an onset of an eating disorder, such as acid reduction, motility problems, or a condition associated with an eating disorder, the IMD 100 may select various portions of the autonomous nerve described herein to stimulate to perform an efferent, an afferent, or an afferent-efferent combination stimulation in order to alleviate the eating disorder. Further, the stimulation target unit 690 is capable of directing the IMD 200 to deliver a sensory stimulus signal to the patient. The sensory stimulus signal may include a pain stimulus, a noxious stimulus, temperature stimulus, and/or any type of sensory stimulus.

The IMD 200 contains a sensory stimulation unit 698 which is capable of generating and delivering stimulation signals to one or more electrodes via leads. A number of leads may be coupled to the sensory stimulation unit 698. A sensory stimulus may be delivered to the leads by the sensory stimulation unit 698 based upon instructions from the controller 610. The sensory stimulation unit 698 may comprise various circuitry, such as stimulation signal generators, impedance control circuitry to control the impedance "seen" by the leads, and other circuitry that receives instructions relating to the type of stimulation to be performed. The sensory stimulation unit 698 is capable of delivering a controlled signal over the leads to a sensory stimulation device.

One or more blocks illustrated in the block diagram of IMD 100 in FIG. 6 may comprise hardware units, software units, firmware units or any combination thereof. Additionally, one or more blocks illustrated in FIG. 6 may be combined with other blocks, which may represent circuit hardware units, software algorithms, etc. Additionally, any number of the circuitry or software units associated with the various blocks illustrated in FIG. 6 may be combined into a programmable device, such as a field programmable gate array, an ASIC device, etc.

Figure 7:
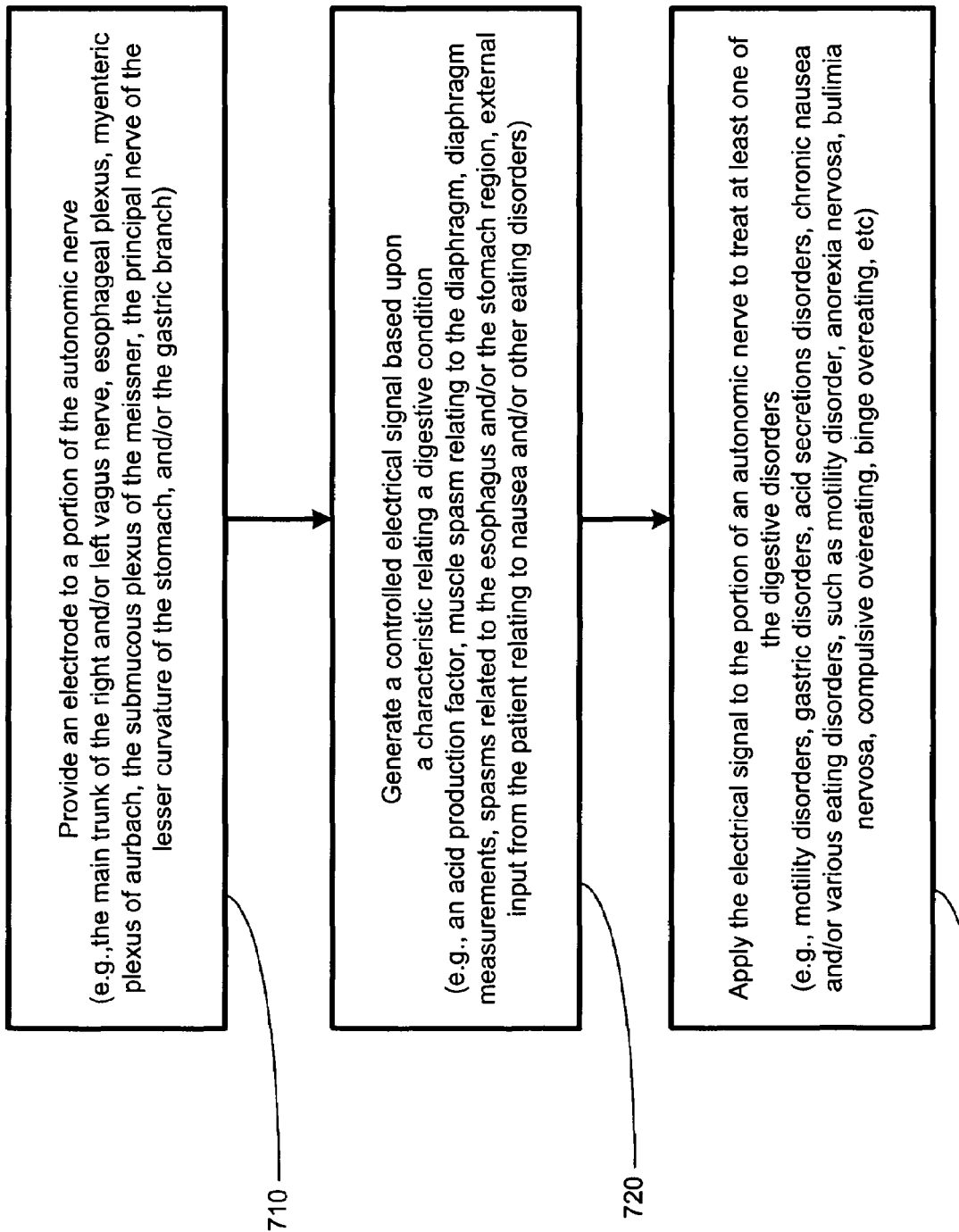
FIG. 7 illustrates a flowchart depiction of a method for treating an eating disease, in accordance with illustrative embodiment of the present invention.

Turning now to FIG. 7, a flowchart depiction of a method for treating an eating disorder, in accordance with one illustrative embodiment of the present invention is provided. An electrode may be coupled to a portion of an autonomous nerve to perform a stimulation function or a blocking function to treat an eating disorder. In one embodiment, one or more electrodes may be positioned in electrical contact or proximate to a portion of the autonomic nerve to deliver a stimulation signal to the portion of the autonomic nerve (block 710). The electrodes may be operatively coupled to at least one of main trunk of the right or left vagus nerve, esophageal plexus 302, myenteric plexus of Auerbach 350, the submucosal plexus of Meissner 360, the principal nerve of the lesser curvature of the stomach, or the gastric branch 307. The IMD 100 may then generate a controlled electrical signal, based upon one or more characteristic relating to the eating disorder(s) of the patient (block 720). This may include a predetermined electrical signal that is preprogrammed based upon a particular condition of a patient, such as data relating to an acid production factor, muscle spasm relating to the diaphragm, diaphragm measurements, spasms related to the esophagus or the stomach region, external input from the patient relating to nausea or other eating disorders, etc. For example, a physician may pre-program the type of stimulation to provide (e.g., efferent, afferent, or afferent-efferent combination stimulation) in order to treat the patient based upon the type of pancreas-related disorder of the patient. The IMD 100 may then generate a signal, such as a controlled-current pulse signal, to affect the operation of one or more portions of the eating system of a patient.

The IMD 100 may then deliver the stimulation signal to the portion of the autonomic nerve, as determined by the factors acid production, muscle spasm relating to the diaphragm, diaphragm measurements, spasms related to the esophagus or the stomach region, external input from the patient relating to nausea or other eating disorders, etc. (block 730). The application of the electrical signal may be delivered to the main trunk of the right or left vagus nerve, esophageal plexus 302, myenteric plexus of Auerbach 350, the submucosal plexus of Meissner 360, the principal nerve of the lesser curvature of the stomach, or the gastric branch 307. In one embodiment, application of the stimulation signal may be designed to promote an afferent effect to either attenuate or increase the activity of urge to eat. Further, the stimulation by the IMD 100 may reduce incidents relating to anorexia nervosa, bulimia nervosa, compulsive overeating, or binge overeating. Additionally, stimulation by the IMD 100 may reduce the conditions brought on by motility disorders, gastric disorders, or acid secretion disorders.

In another embodiment, application of the stimulation signal may be designed to promote a blocking effect relating to a signal that is being sent from the brain to the various portions of the eating system to treat the eating disorder. For example, chronic nausea may be diminished by blocking various signals from the brain to the various portions of the pancreas. This may be accomplished by delivering a particular type of controlled electrical signal, such as a controlled current signal to the autonomic nerve. In yet another embodiment, afferent fibers may also be stimulated in combination with an efferent blocking to treat an eating disorder.

Additional functions, such as a detection process, may be alternatively employed with the embodiment of the present invention. The detection process may be employed such that an external detection or an internal detection of a bodily function may be used to adjust the operation of the IMD 100.

Figure 8:
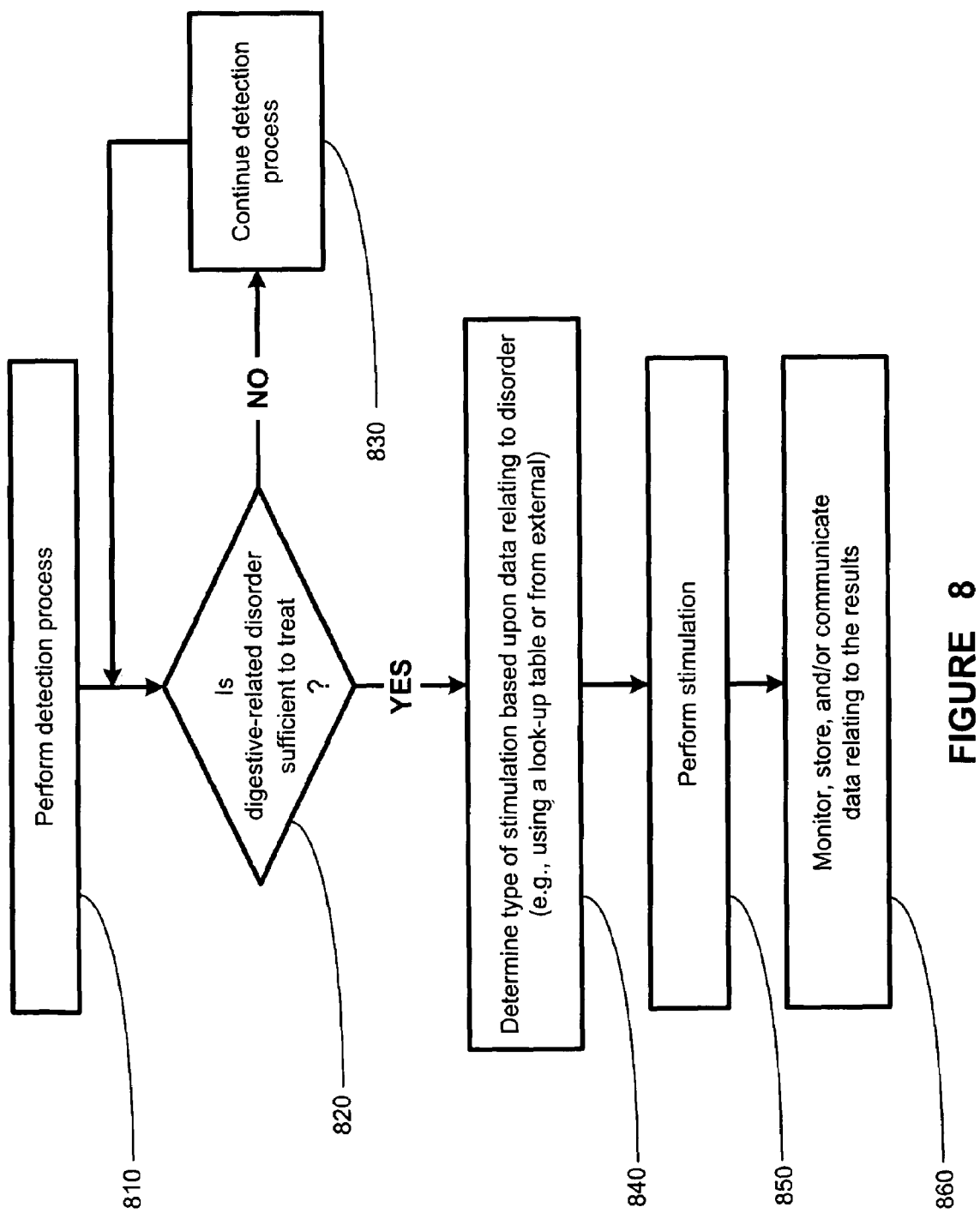
FIG. 8 illustrates a flowchart depiction of an alternative method for treating an eating disease, in accordance with an alternative illustrative embodiment of the present invention.

Turning now to FIG. 8, a block diagram depiction of a method in accordance with an alternative embodiment of the present invention is illustrated. The IMD 100 may perform a database detection process (block 810). The detection process may encompass detecting a variety of types of characteristics of the gastrointestinal activity, an acid production factor, muscle spasm relating to the diaphragm, diaphragm measurements, spasms related to the esophagus or the stomach region, external input from the patient relating to nausea or other eating disorders, etc. A more detailed depiction of the steps for performing the detection process is provided in FIG. 9, and accompanying description below. Upon performing the detection process, the IMD 100 may determine whether a detected eating disorder is sufficiently severe to treat based upon the measurements performed during the detection process (block 820). For example, the muscle spasm relating to the diaphragm may be examined to determine whether it is greater than a predetermined value where intervention by the IMD 100 is desirable. Upon a determination that the disorder is insufficient to treat by the IND 100, the detection process is continued (block 830).

Upon a determination that the disorder is sufficient to treat using the IMD 100, a determination as to the type of stimulation based upon data relating to the disorder is made (block 840). The type of stimulation may be determined in a variety of manners, such as performing a look-up in a look-up table that may be stored in the memory 617. Alternatively, the type of stimulation may be determined by an input from an external source, such as the external unit 670 or an input from the patient. Further, determination of the type of stimulation may also include determining the location as to where the stimulation is to be delivered. Accordingly, the selection of particular electrodes, which may be used to deliver the stimulation signal, is made. A more detailed description of the determination of the type of stimulation signal is provided in FIG. 10 and accompanying description below.

Upon determining the type of stimulation to be delivered, the IMD 100 performs the stimulation by delivering the electrical signal to one or more selected electrodes (block 850). Upon delivery of the stimulation, the IMD 100 may monitor, store, or compute the results of the stimulation (block 860). For example, based upon the calculation, a determination may be made that adjustment(s) to the type of signal to be delivered for stimulation, may be performed. Further, the calculations may reflect the need to deliver additional stimulation. Additionally, data relating to the results of stimulation may be stored in memory 617 for later extraction or further analysis. Also, in one embodiment, real time or near real time communications may be provided to communicate the stimulation result or the stimulation log to an external unit 670.

Figure 9:
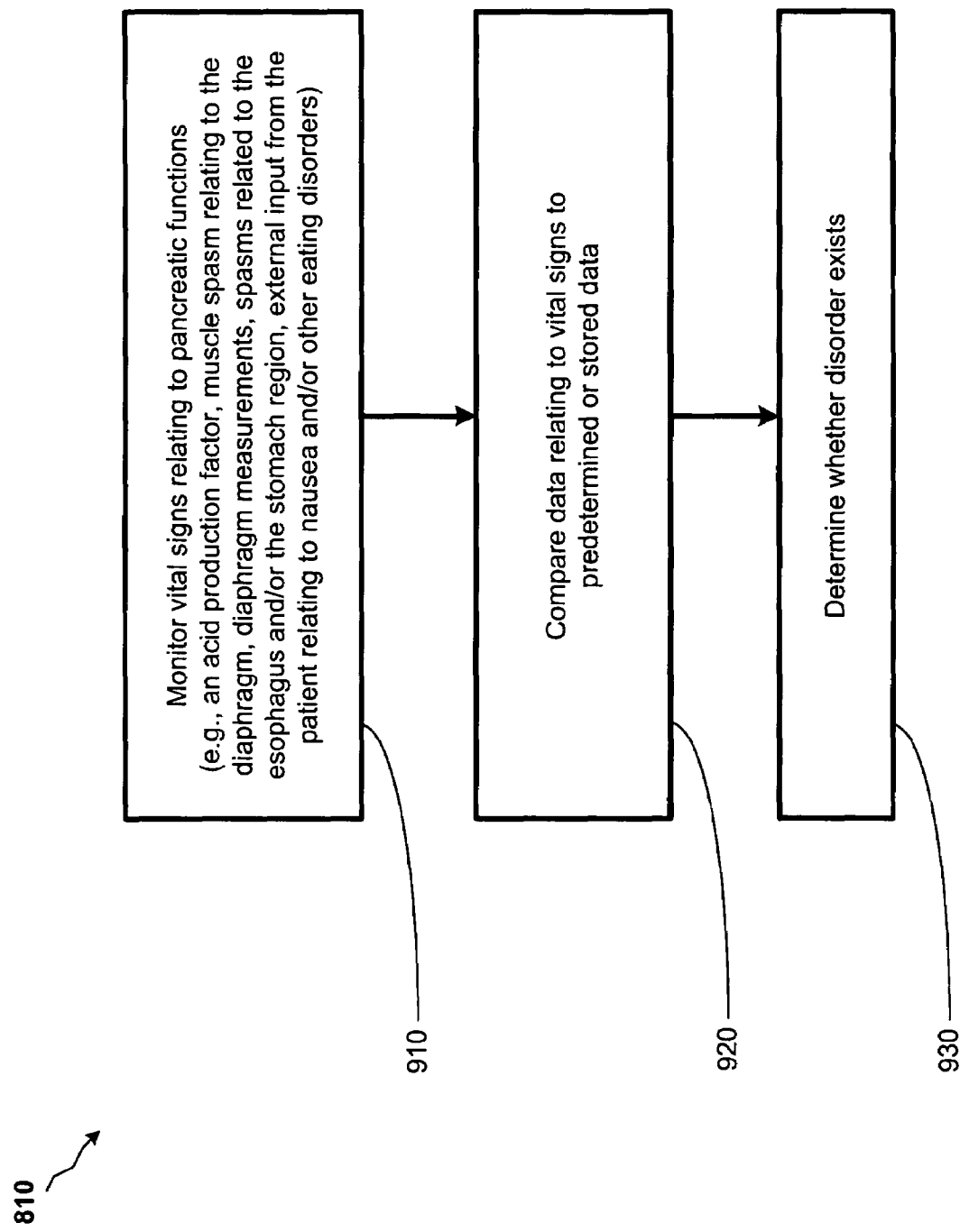
FIG. 9 depicts a more detailed flowchart depiction of step of performing a detection process of FIG. 8, in accordance with an illustrative embodiment of the present invention.

Turning now to FIG. 9, a more detailed block diagram depiction of the step of performing the detection process of block 810 in FIG. 8, is illustrated. The system 100 may monitor one or more vital signs relating to the eating functions of the patient (block 910). For example, factors relating to an acid production, muscle spasm relating to the diaphragm, diaphragm measurements, spasms related to the esophagus or the stomach region, external input from the patient relating to nausea or other eating disorders, etc., may be detected. This detection may be made by sensors residing inside the human body, which may be operatively coupled to the IMD 100. In another embodiment, these factors may be performed by external means and may be provided to the IMD 100 an external device via the communication system 660.

Upon acquisition of various vital signs, a comparison may be performed comparing the data relating to the vital signs to predetermined, stored data (block 920). For example, the muscle spasm levels may be compared to various predetermined thresholds to determine whether aggressive action would be needed, or simply further monitoring would be sufficient. Based upon the comparison of the collected data with theoretical, stored thresholds, the IMD 100 may determine whether a disorder exists (block 930). For example, various vital signs may be acquired in order to determine afferent or efferent stimulation fibers are to be stimulated. Based upon the determination described in FIG. 9, the IMD 100 may continue to determine whether the disorder is sufficiently significant to perform treatment, as described in FIG. 8.

Figure 10:
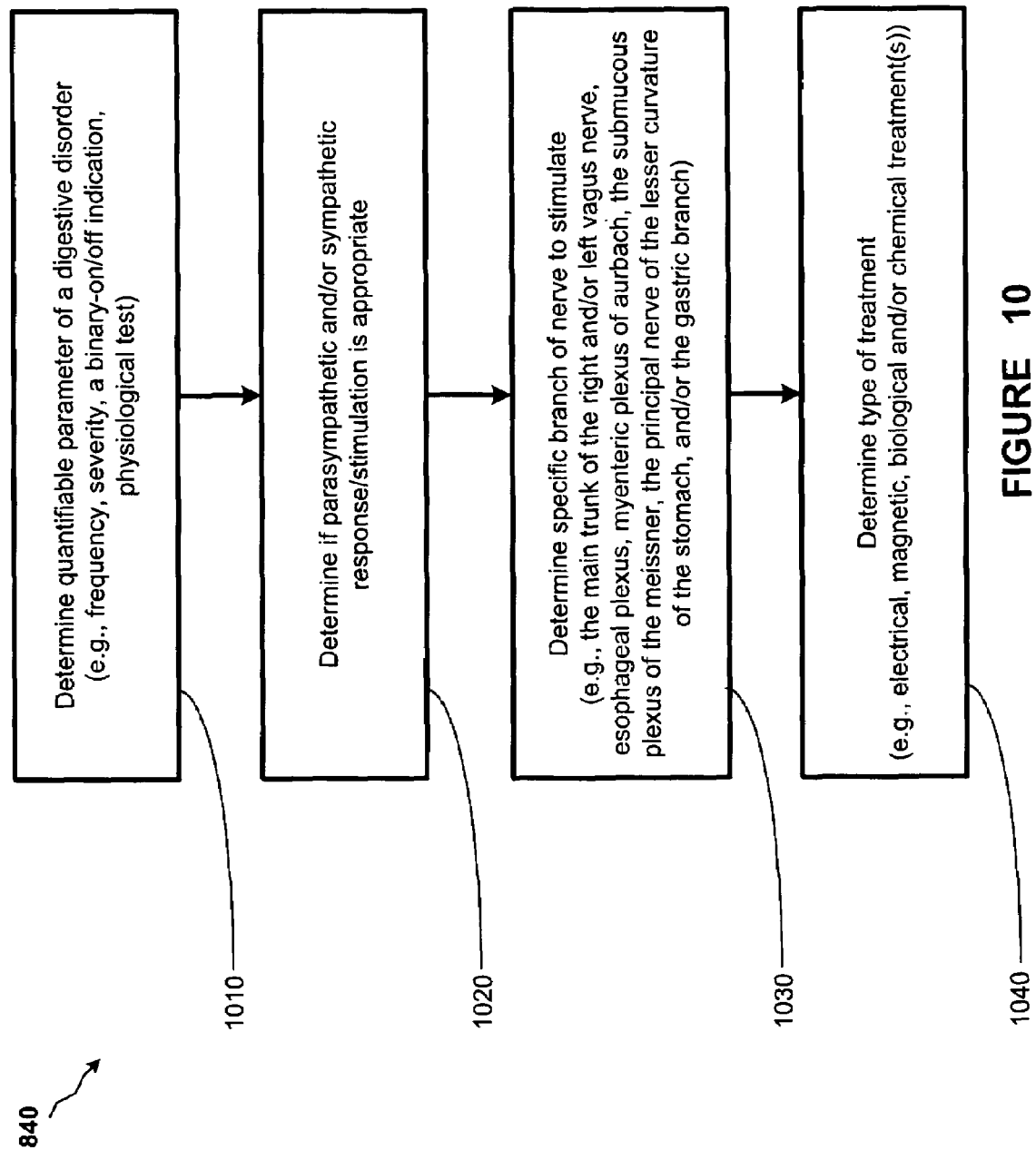
FIG. 10 depicts a more detailed flowchart depiction of the steps of determining a particular type of stimulation based upon data relating to an eating disorder described in FIG. 8, in accordance with an illustrative embodiment of the present invention.

Turning now to FIG. 10, a more detailed flowchart depiction of the step of determining the type of stimulation indicated in block 840 of FIG. 8, is illustrated. The IMD 100 may determine a quantifiable parameter of an eating disorder (block 1010). These quantifiable parameters, for example, may include a frequency of occurrence of various symptoms of an eating disorder, e.g., an acid production factor, muscle spasm relating to the diaphragm, diaphragm measurements, spasms related to the esophagus or the stomach region, external input from the patient relating to nausea or other eating disorders. Based upon these quantifiable parameters, a determination may be made whether a parasympathetic or a sympathetic response/stimulation is appropriate (block 1020). For example, as illustrated in Table 2, a matrix may be used to determine whether a parasympathetic or a sympathetic response for stimulation is appropriate. This determination may be overlaid by the decision regarding whether an efferent, an afferent, or an efferent-afferent combination stimulation should be performed.

TABLE 2

|  | EFFERENT | AFFERENT | EFFERENT-AFFERENT |
|---|---|---|---|
| PARASYMPATHETIC | Yes | No | No |
| SYMPATHETIC | Yes | Yes | Yes |

The example illustrated in Table 2 shows that an efferent, parasympathetic stimulation is to be provided in combination with a sympathetic, efferent-afferent combination stimulation for a particular treatment. A determination may be made that for a particular type of quantifiable parameter that is detected, the appropriate treatment may be to perform a parasympathetic blocking signal in combination with a sympathetic non-blocking signal. Other combinations relating to Table 2 may be implemented for various types of treatments. Various combinations of matrix, such as the matrix illustrated in Table 2 may be stored in the memory for retrieval by the IMD 100.

Additionally, external devices may perform such calculation and communicate the results or accompanying instructions to the IMD 100. The IMD 100 may also determine the specific batch of the nerve to stimulate (block 1030). For example, for a particular type of stimulation to be performed, the decision may be made to stimulate the main trunk of the right or left vagus nerve, esophageal plexus 302, the myenteric plexus of Auerbach 350, the submucosal plexus of Meissner 360, the principal nerve of the lesser curvature of the stomach, or the gastric branch 307. The IMD 100 may also indicate the type of treatment to be delivered. For example, an electrical treatment alone or in combination with another type of treatment may be provided based upon the quantifiable parameter(s) that are detected (block 1040). For example, a determination may be made that an electrical signal by itself is to be delivered. Alternatively, based upon a particular type of disorder, a determination may be made that an electrical signal, in combination with a magnetic signal, such as transcranial magnetic stimulation (TMS) may be performed. Stimulation can be induced by light such as from a laser.

In addition to electrical or magnetic stimulation, a determination may be made whether to deliver a chemical, biological, or other type of treatment(s) in combination with the electrical stimulation provided by the IMD 100. In one example, electrical stimulation may be used to enhance the effectiveness of a chemical agent, such as nausea-reducing drug. Therefore, various drugs or other compounds may be delivered in combination with an electrical stimulation or a magnetic stimulation. Based upon the type of stimulation to be performed, the IMD 100 delivers the stimulation to treat various eating disorders.

Using embodiments of the present invention, various types of stimulation may be performed to treat gastrointestinal-related disorders, such as bulimia. For example, motility disorders, gastric disorders, acid secretions disorders, chronic nausea or various eating disorders (e.g., motility disorder, anorexia nervosa, bulimia nervosa, compulsive overeating, binge overeating, etc), may be treated by performing autonomic nerve stimulation. The autonomic stimulation of embodiments of the present invention may include stimulation of the portions of a vagus nerve or sympathetic nerves, such as the nerves residing in the esophagus plexus 302. Embodiments of the present invention provide for performing preprogrammed delivery of stimulation or performing real time decision-making to deliver controlled stimulation. For example, various detections of parameters, such as factors relating to an acid production factor, muscle spasm relating to the diaphragm, diaphragm measurements, spasms related to the esophagus or the stomach region, external input from the patient relating to nausea or other eating disorders, may be used to determine whether a stimulation is needed or the type of stimulation that is to be delivered. Parasympathetic, sympathetic, blocking, non-blocking, afferent, or efferent delivery of stimulation may be performed to treat various eating disorders.

In one embodiment, the present invention relates to a method for treating an eating disorder comprising coupling at least one electrode to at least one vagus nerve of the patient, implanting a sensory stimulation device in the patient, applying a sensory stimulus to the patient using the sensory stimulation device, detecting the patient's response to the sensory stimulus, and applying an electrical signal to the vagus nerve using the electrode after detecting the response to treat the eating disorder.

The sensory stimulation device may be any device that can provide a sensory stimulus. Exemplary sensory stimuli include a noxious stimulus, a pain stimulus, or a temperature stimulus, among others. The sensory stimulation device may provide one or more than one type of sensory stimulus. Independently, it may provide varying intensities of one or more than one type of sensory stimulus.

In the case of bulimia, there generally exists for many patients a positive correlation between pain threshold and binge/purge episodes. Though not to be bound by theory, a higher pain threshold (or lower sensitivity to pain) may reflect, either directly or indirectly, a perturbation in the patient's satiety signaling mechanism; a patient whose brain is unable to receive or process a satiety signal may be more likely to eat past the point of normal fullness. By applying a sensory stimulus, a response indicative of the patient's pain threshold at that time will be generated. It has been observed that bulimic patients often feature cyclicality in their pain sensitivity or pain threshold with sensitivity troughs or threshold peaks occurring at or around the time of binge/purge episodes. See, e.g., Raymond N C, de Zwaan M, Faris P L, Nugent S M, Achard D M, Crosby R D, Mitchell J E., Pain thresholds in obese binge-eating disorder subjects, Biol Psychiatry. 1995 Feb. 1; 37(3):202-4; Raymond N C, Eckert E D, Hamalainen M, Evanson D, Thuras P D, Hartman B K, Faris P L., A preliminary report on pain thresholds in bulimia nervosa during a bulimic episode., Compr Psychiatry. 1999 May-June; 40(3):229-33.

Detecting the patient's response to the sensory stimulus can be performed by one or more of a number of techniques. A sensor of an autonomic response to the sensory stimulus (such as heart rate, respiration rate, myoelectric signals from the stomach/abdomen using electrogastrogram (EGG), heart rate variability (HRV), respiratory sinus arrhythmia (RSA), evoked potentials in the brain detected by EEG, detect vagal hypersensitivity or hyperactivity by measuring action potentials on the nerve with the sensing electrode, or sense satiety signals, among other responses) can detect the response and report it to a controller, such as controller 155 in IMD 100. A physician or other observer can gauge the patient's response to the sensory stimulus and record his or her observation. The patient can record the perceived intensity of the sensory stimulus. Recording of observations by a person can be performed on a handheld computer or similar device (such as a cellular telephone or PDA, among others) and can be reported to a controller, such as controller 155 in IMD 100. The controller can analyze the sensory stimulus and the reported patient response thereto and compare those values to a baseline of patient responses to sensory stimuli. The baseline of patient responses can have been previously prepared by the physician and the patient at around the time the IMD 100 was implanted. If the reported patient response, as compared to baseline, indicates the patient's pain threshold has increased (i.e., a sensory stimulus having a first intensity value according to the patient's baseline is perceived as having a lower, second intensity value at a particular time), the controller can adjust the parameters of cranial nerve stimulation to a parameter set useful in reducing the intensity or the duration of binge/purge episodes.

EGG, similar to an electrocardiogram (EKG) of the heart, can record the electrical signals that travel through the muscles of the stomach controlling the muscles' contractions. Additionally, EGG can measure stomach wall nerve activity before and after food ingestion. Contemporary EGG systems can record on up to four channels simultaneously, allowing for complete activity recording in a short time frame. EGG can be an appropriate diagnostic tool when there is a suspicion that the nerves controlling stomach muscles or the stomach muscles themselves are not working normally. EGG can be used for a variety of gastrointestinal motility disorders or for patients with no known GI disorder who are suffering from unexplained nausea. EGG can identify dysrhythmias, especially after meals, in patients with gastroparesis, chronic dyspepsia, anorexia nervosa and bulimia, cyclic vomiting syndrome, and other conditions characterized by a delayed gastric emptying.

In treating bulimia, a plurality of parameter sets for cranial nerve stimulation can be used. A first parameter set can be used during periods of low pain threshold and correlated low risk of a binge/purge episode. A second or acute parameter set, as discussed above, can be used during periods of high pain threshold and correlated high risk of a binge/purge episode to reduce the intensity or the duration of such an episode. In one embodiment, a third parameter set can be used during the patient's sleep. Adjustment of cranial nerve stimulation parameters to the third parameter set can be performed manually by the patient or can be automatically performed by detection of low motion or horizontal orientation by the patient by a sensor capable of detecting such states. Such a sensor can be implanted in the patient directly, enclosed in an IMD 100, or be placed external to the patient.

Activation of an acute parameter set for cranial nerve stimulation can also be performed manually by the patient or others who perceive an incipient binge/purge episode or prophylactically prior to a normal eating episode. Techniques for manual activation are described above.

In one embodiment, wherein the treatment stimulus and the sensory stimulus can be provided by the same electrode and electrode assembly, the treatment stimulus and sensory stimulus could be the same (same parameters delivering electrical stimulation at the same electrode on the nerve) and the treatment stimulus and the sensory stimulus could be interleaved, i.e. by applying a treatment stimulus sequence during a treatment period, then applying a short burst of sensory stimulus to determine if the patient's pain threshold has been exceeded. If the sensory stimulus exceeds the patient's tolerance level, then nerve stimulation parameters can be adjusted using a magnet (or other adjustment device, such as a tap sensor) to activate the pulse generator program.

In one embodiment, detection of a patient's point on the bulimic cycle can be performed by applying a stimulus to a first location in the body, detecting at least one response selected from the group consisting of refractory period, latency, synaptic latency, synaptic jitter, and conduction delay resulting from said stimulus to a second location in the body, and comparing the measured parameter to a baseline.

A refractory period may refer to the short time immediately after an action potential in which the neuron cannot respond to another stimulus, owing to an increase in potassium permeability.

A conduction delay may refer to the delay in the transmission of action potentials due to factors such as synaptic inhibition, neural damage, ion depletion. When neurons communicate over some distance, there are conduction delays between the firing of the presynaptic neuron and the receipt of the signal at the postsynaptic cell.

A latency may refer to the period of apparent inactivity between the time the stimulus is presented and the moment a response occurs.

A synaptic latency may refer to the time between stimulus delivery and appearance of the synaptic event in a pathway, and is generally thought to be directly related to the complexity of that pathway. Synaptic jitter is used herein as shock-to-shock variability in synaptic latency.

In an alternative embodiment, the detection of a patient's point on the bulimic cycle may be performed by sensing a physiological parameter, such as hormone concentration or neurotransmitter concentration, among others, using a physiological parameter sensor implanted at or capable of calculating data from a location in the body and comparing the measured parameter to a baseline.

In yet another embodiment, detection and recording of a patient's pain threshold over time can provide a diagnostic indication of patient therapy benefit. For example, a decrease in the patient's pain threshold over time may be indicative of beneficial therapy.

In one embodiment, the patient may use a patient recording device, such as a handheld computer, to store diary information related to the disorder for diagnosis or treatment modification. The patient may enter such information as date, time, frequency, intensity, or duration of hunger urges; date, time, frequency, intensity, or duration of eating episodes; date, time, frequency, intensity, or duration of binge/purge episodes; quantity of food intake; mood changes; or lifestyle events, among others. The diary program executed by the handheld computer can be structured to allow easy quantification of subjective and qualitative information. The diary program can analyze the data to determine if changes in the patient's cranial nerve stimulation parameter set(s) are appropriate and communicate with the controller to effect such changes. The diary program can communicate with a physician to provide patient status information between regularly scheduled examinations.

Figure 11:
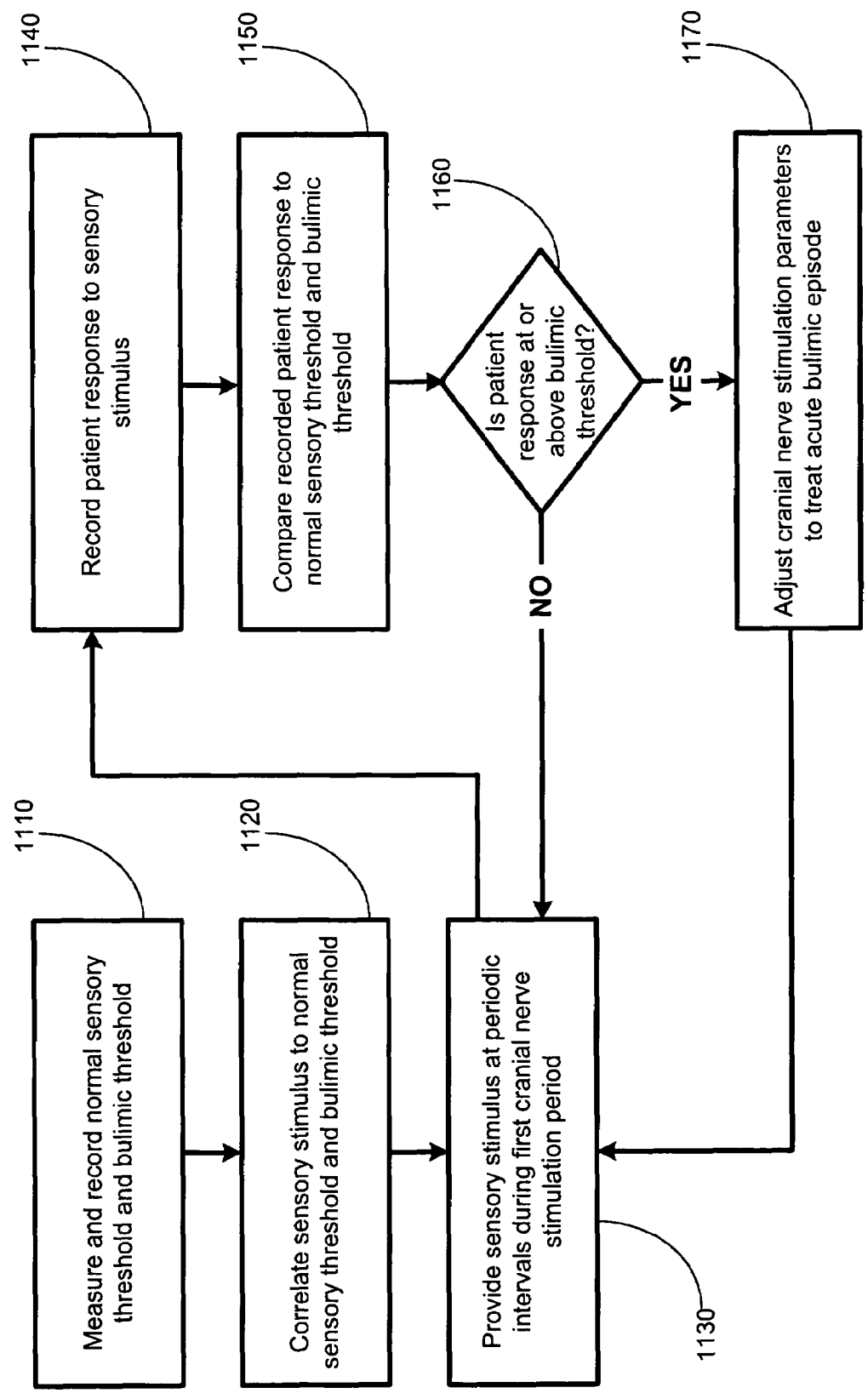
FIG. 11 illustrates a flowchart depiction of a method for treating an eating disease, in accordance with illustrative embodiment of the present invention.

Turning now to FIG. 11, a flowchart depiction of a method for treating an eating disorder, in accordance with one illustrative embodiment of the present invention is provided. A patient's normal sensory threshold and bulimic threshold to the same stimulus is measured and recorded (block 1110). A particular intensity of the sensory stimulus can be correlated with the normal sensory threshold and the bulimic threshold of the patient (block 1120).

Armed with the foregoing knowledge and using a system such as that shown in FIG. 6, a sensory stimulus of a known intensity can be provided to the patient at periodic intervals during a first cranial nerve stimulation period when a bulimic episode is not taking place (block 1130). The periodic intervals can be in the range of 1 min to 6 hr, such as in the range of 1 hr to 3 hr. The patient's response, as measured by a sensor or noted by the patient, is recorded (block 1140). The recorded response can then be compared to the patient's normal sensory threshold and bulimic threshold (block 1150). Generally speaking, the patient's normal sensory threshold will be below the bulimic threshold and a sensory stimulus that is at or above the bulimic threshold will indicate the likelihood of a bulimic episode in the near future. At the decision point shown in block 1160, if the patient response is below the bulimic threshold, the likelihood of a bulimic threshold is low and the first cranial nerve stimulation period can continue (flow from block 1160 to block 1130). If the patient response is at or above the bulimic threshold, the process flows to block 1170, wherein the cranial nerve stimulation parameters are adjusted to treat an acute bulimic episode, such as by increasing pulse amplitude, pulse duration, or other parameters as described above. The duration of treating the acute bulimic episode can be preprogrammed, can be given to the control of the patient, or can be determined by other means. After treating the acute bulimic episode is over, the first cranial nerve stimulation period can be resumed (block 1130).

Figure 12:
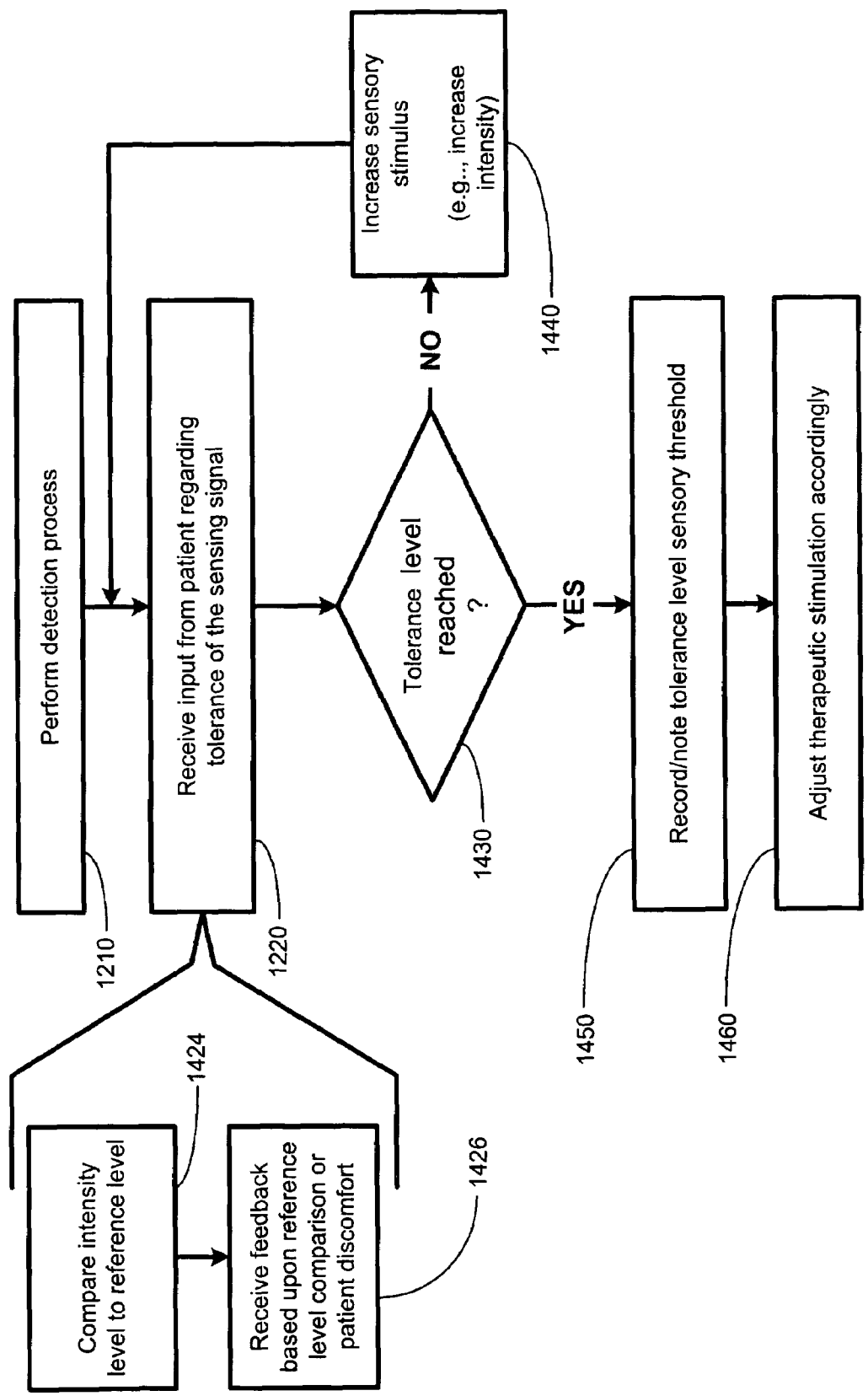
FIG. 12 illustrates a flowchart depiction of a method for treating an eating disease, in accordance with an alternative illustrative embodiment of the present invention.

Turning now to FIG. 12, a flowchart depiction of an alternative embodiment for treating an eating disorder, in accordance with one illustrative embodiment of the present invention is provided. A sensory stimulus at an initial intensity may be provided to a cranial nerve of the patient (block 1210). The sensory stimulus may include a noxious stimulus, temporary pain discomfort, temperature increase, or other sensory stimulus.

Based upon the sensory stimulus, feedback input from the patient and/or a sensor relating to the tolerance of the discomfort caused by the sensory signal may be received. (block 1220). The feedback process of block 1220 may include comparing the intensity level of a stimulus signal to a predetermined reference level (block 1224). The feedback may include physiological thresholds, such as pain, noxious feeling, and/or other sensory, somatosensory, somatic, and/or visceral sensations. The step described in block 1220 may also include receiving feedback based upon the reference level comparison or the patient discomfort caused by the sensory signal. (block 1226). For example, an intensity of a noxious feeling caused by a noxious stimulus may be compared to a baseline noxious detection.

In response to the feedback received from the patient, a determination may be made as to whether the tolerance level of the patient has been reached as a result of the sensory signal. (block 1230). If a determination is made that the tolerance level has not yet been reached, an increase in the sensory stimulus intensity may be provided. (block 1240). Subsequently, the feedback path (blocks 1220, 1224, 1226, 1230, and 1240 of FIG. 4) is repeated until the threshold level (block 4130) has been reached. Upon reaching the threshold level, the tolerance level (i.e., the sensory threshold), is then recorded (block 1250). Based upon the sensory threshold, subsequent therapeutic stimulation may be adjusted (block 1260). The adjustment process may include decreasing a non-stimulation time period. In other words, the frequency of the stimulation periods may be adjusted. Other adjustments, such as the intensity of the stimulation, pulse widths, frequency of pulse, etc., may be performed. Adjustments to the therapeutic signal stimulation may also be based upon various other feedbacks that may be detected, such CCK (cholecystokinin) indications and/or other chemical or biological indications in the patient's body.

Figure 13:
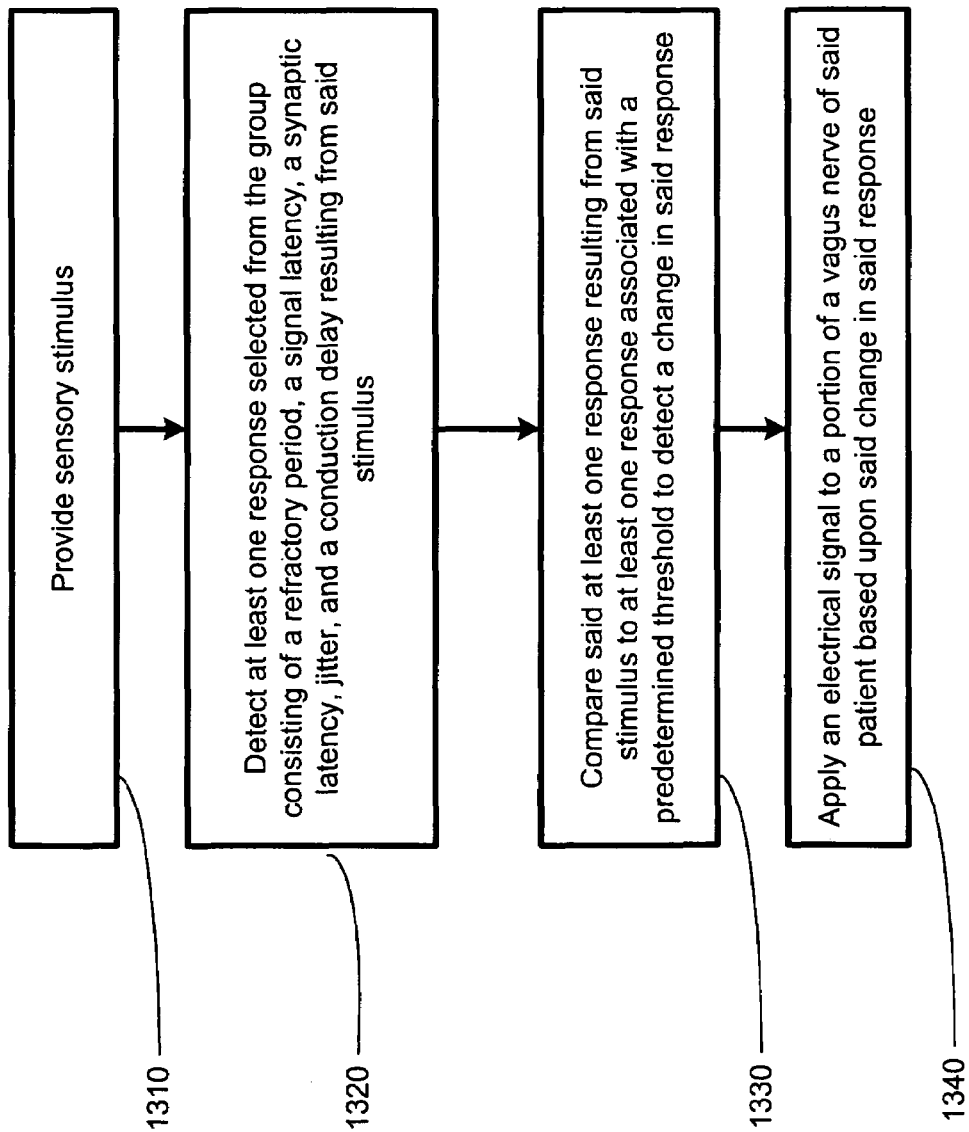
FIG. 13 illustrates a flowchart depiction of a method for treating an eating disease, in accordance with yet another alternative illustrative embodiment of the present invention.

Turning now to FIG. 13, an alternative embodiment of utilizing a feedback for adjusting stimulation to treat an eating disorder, in accordance with one illustrative embodiment of the present invention is provided. A sensory stimulus may be provided to a portion of the cranial nerve of the patient (block 1310). The implementation of the sensory stimulation may affect the synaptic plasticity, which may affect at least one response selected from the group consisting of a refractory period, a signal latency, a synaptic latency, jitter, and a conduction delay. Upon delivery of the sensory stimulus, the at least one response selected from the group consisting of a refractory period, a signal latency, a synaptic latency, jitter, and a conduction delay of the signal traveling in proximity to the stimulated portion of the cranial nerve may be detected (block 1320). Based upon the period of the at least one response, a comparison is made to corresponding factors associated with a predetermined threshold (block 1330). The predetermined threshold of the at least one response may be a measured factor or a calculated factor. Data regarding the at least one response relating to a predetermined threshold may be pre-recorded.

The comparison between the period of the at least one response to corresponding factors associated with a predetermined threshold may reveal a change in the response. Based upon the changes in the at least one response, a nerve synaptic transmission efficacy may be determined. Reflex excitability is a measure of synaptic transmission efficacy derived from muscle or nerve response as determined by an electromyogram. Based upon the nerve synaptic transmission efficacy, a correlation between the changed nerve synaptic transmission efficacy and a state or intensity of the disorder may be performed. In other words, an abnormal nerve synaptic transmission efficacy is correlated to a particular state of an eating disorder episode, such as bulimia. Based on the information relating to the synaptic transmission efficacy to particular intensities of the disorder, an electrical signal may be applied to a portion of a vagus nerve of said patient based upon said change in said response (block 1340). In other words, a determination may be made as to the probability of a certain type of disorder episode of particular intensity occurring in the near future. Based upon this determination, a correlated efficacy may then be used to increase or decrease the therapeutic stimulation. In this manner, changes in the efficacy of the nerve synaptic transmission may be used to adjust therapeutic stimulation, which is then tailored to the particular type of episode detected or predicted to occur in the patient's body.

Other types of feedback may also be used to adjust the therapeutic stimulation used to treat eating disorders. For example, a long-term type of feedback, such as data entered into a patient programmer, a chart, or a diary may be used to store information for diagnostic purposes. This information may include various indications, such as the intensity (e.g. high, moderate, low) of a hunger urge, as well as the date and time corresponding to such urges. This information may be used to calculate the actual and/or predicted frequency of such intensity and urges. Similarly, like information may also be gathered for the eating habits, such as meal size (e.g., large meals, moderate meals, small meals, etc), the date and time, and the frequency of such events. Further, mood stage changes, such as severe depression, moderate depression, etc., along with the respective durations, may then also be recorded. These tabulations may be correlated to major life changes that may affect any of the factors described above. The long-term feedback data described above then may be diagnostically analyzed and adjustments to various device parameters or therapeutic treatments may then be performed.

All of the methods and apparatus disclosed and claimed herein may be made and executed without undue experimentation in light of the present disclosure. While the methods and apparatus of this invention have been described in terms of particular embodiments, it will be apparent to those of skill in the art that variations may be applied to the methods and apparatus and in the steps or in the sequence of steps of the method described herein without departing from the concept, spirit and scope of the invention as defined by the appended claims. It should be especially apparent that the principles of the invention may be applied to selected cranial nerves other than the vagus nerve to achieve particular results.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method of treating a patient having an eating disorder using an implantable medical device, comprising:
    applying a stimulus to said patient using said implantable medical device;
    detecting at least one response selected from the group consisting of a refractory period, a signal latency, a synaptic latency, a synaptic jitter, and a conduction delay resulting from said stimulus;
    comparing said at least one response resulting from said stimulus to at least one response associated with a predetermined threshold to detect a change in said response; and
    applying an electrical signal to a portion of a vagus nerve of said patient based upon said change in said response, for treating an eating disorder of the patient.

2. The method of claim 1, wherein detecting said refractory period comprises detecting a time period after an action potential is induced in a nerve of the patient.

3. The method of claim 1, wherein detecting said conduction delay comprises measuring a time period between the neuronal transmission of an action potential in a nerve of the patient and the arrival of a resultant signal at a target location corresponding to said neuronal transmission.

4. The method of claim 1, wherein detecting said signal latency comprises detecting a time period of apparent inactivity between the time a stimulus signal is applied and the time a response occurs.

5. The method of claim 4, wherein detecting said synaptic jitter comprises detecting variability in said latency of neuronal transmission.

6. The method of claim 1, wherein detecting said synaptic latency comprises detecting a time period between delivery of a stimulus signal and the arrival of the synaptic event at a target location.

7. The method of claim 1, wherein said stimulus is selected from the group consisting of a noxious stimulus, a pain stimulus, a temperature stimulus, and a discomfort stimulus.

* * * * *